US006860266B2

(12) United States Patent
Blike

(10) Patent No.: US 6,860,266 B2
(45) Date of Patent: Mar. 1, 2005

(54) PHYSIOLOGICAL OBJECT DISPLAYS

(75) Inventor: George T. Blike, Norwich, VT (US)

(73) Assignee: Dartmouth-Hitchcock Clinic, Lebanon, NH (US)

( * ) Notice: Subject to any disclaimer, the term of this patent is extended or adjusted under 35 U.S.C. 154(b) by 0 days.

(21) Appl. No.: 10/054,069

(22) Filed: Jan. 22, 2002

(65) Prior Publication Data
US 2003/0191373 A1 Oct. 9, 2003

Related U.S. Application Data

(63) Continuation-in-part of application No. 09/706,512, filed on Nov. 3, 2000, now Pat. No. 6,743,172.
(60) Provisional application No. 60/263,861, filed on Jan. 23, 2001.

(51) Int. Cl.[7] .............................................. A62B 17/00
(52) U.S. Cl. ................................................. 128/205.23
(58) Field of Search .................................. 128/205.23

(56) References Cited

U.S. PATENT DOCUMENTS

| 3,811,040 | A | | 5/1974 | Weinfurt et al. | |
|---|---|---|---|---|---|
| 4,562,843 | A | | 1/1986 | Djordjevich et al. | ......... 128/672 |
| 5,101,825 | A | | 4/1992 | Gravenstein et al. | ....... 128/633 |
| 5,183,051 | A | | 2/1993 | Kraidin et al. | ............... 128/687 |
| 5,217,019 | A | | 6/1993 | Hughes | ........................ 128/668 |
| 5,231,981 | A | * | 8/1993 | Schreiber et al. | ....... 128/205.23 |
| 5,262,944 | A | | 11/1993 | Weisner et al. | ............. 600/300 |
| 5,297,552 | A | | 3/1994 | Mignot | |
| 5,316,005 | A | | 5/1994 | Tomita | ......................... 600/500 |
| 5,398,680 | A | | 3/1995 | Polson et al. | ................ 126/633 |
| 5,546,943 | A | | 8/1996 | Gould | |
| 5,551,434 | A | | 9/1996 | Iinuma | |
| 5,701,897 | A | | 12/1997 | Sano | |
| 5,921,920 | A | | 7/1999 | Marshall et al. | ............. 600/300 |
| 5,931,160 | A | * | 8/1999 | Gilmore et al. | ........ 128/204.21 |
| 6,024,089 | A | * | 2/2000 | Wallace et al. | ......... 128/204.21 |
| 6,234,963 | B1 | | 5/2001 | Blike et al. | ................. 600/300 |
| 6,543,449 | B1 | * | 4/2003 | Woodring et al. | ...... 128/204.18 |

FOREIGN PATENT DOCUMENTS

| EP | 0059868 | 9/1982 |
|---|---|---|
| EP | 0505037 | 2/1992 |
| EP | 0901798 | 6/1998 |
| JP | 10094519 | 4/1998 |
| WO | 9423643 | 10/1974 |
| WO | 9004353 | 5/1990 |
| WO | 9007357 | 7/1990 |
| WO | 9211804 | 7/1992 |
| WO | 9720592 | 6/1997 |
| WO | WO 99/38433 | 8/1999 |

OTHER PUBLICATIONS

Cole, et al. "Human Performance Evaluation of a Metaphor Graphic Display for Respiratory Data" Methods of Information in Medicine 33: 390–396 (1994).

Cole, et al. "Metaphor Graphics to Support Integrated Decision Making with Respiratory Data" Int'l J. of Clin. Monitoring & Computing 10: 91–100 (1993).

(List continued on next page.)

Primary Examiner—Robert L. Nasser
(74) Attorney, Agent, or Firm—Hinckley, Allen & Snyder LLP

(57) ABSTRACT

The disclosed invention relates to systems and methods for obtaining physiological information from patients and displaying that information in an intuitive and logical format to a physician. Object displays are disclosed that are capable of visually displaying critical information in real time to allow physicians to quickly perceive the importance of changing patient values.

15 Claims, 26 Drawing Sheets

OTHER PUBLICATIONS

Cole, William "Quick and Accurate Monitoring Via Metaphor Graphics" Proceedings of SCAMC (Abstract): 425–429 (1990).

Weinger, et al. "Vigilance, Alarms, and Integrated Monitoring Systems" Anesthesia Equipment, 17: 350–384, Ehrenwerth, et al. Eds. (1993).

Fan, et al. "Effects of Hematocrit Variations on Regional Hemodynamics and Oxygen Transport in the Dog" Am. J. Physiol. 238: H545–H552 (1980).

Lundsgaard–Hansen, P. "Hemodilution–New Clothes for an Anemic Emperor" Vox Sang 36: 321–336 (1979).

Lundsgaard–Hansen, et al. "Is There a Generally Valid, Minimum Acceptable Hemoglobin Level?" Infusionstherapie 16: 167–175 (1989).

Robertie, et al. "Safe Limits of Isovolemic Hemodilution and Recommendations For Erythrocyte Transfusion" Int'l Anesthesiology Clinics 28(4): 197–204 (1990).

Severinghaus, John "Blood Gas Calculator" J. Appl. Physiol. 21(3): 1108–1116 (1966).

Hint, H. The Pharmacology of Dextran and the Physiological Background for the Clinical Use of Rheomacrodex and Macrodex: Acta Anaesthesiologica Belgica 2:119–138 (1968).

Kelman, G. Richard "Digital Computer Subroutine for the Conversion of Oxygent Tension into Saturation" J. Appl. Physiol. 21(4): 1375–1376 (1966).

Mohsenifar, et al. "Relationship Between $O_2$ Delivery and $O_2$ Consumption in the Adult Respiratory Distress Syndrome" Chest 84(3): 267–271 (1983).

Shibutani, et al. "Critical Level of Oxygen Delivery in Anesthetized Man" Critical Care Med. 11(8): 640–643 (1983).

Faithfull, et al. "A Program to Calculate Mixed Venous Oxygen Tension–A Guide to Transfusion?" *Oxygen Transport to Tissue XVI*, Eds. Hogan, et al. pp. 41–49 (1994).

Product Brochure from Waters Instruments, Inc., Rochester, MN 55903–6117 for MRM™ 6000 Metabolic Analyzer in 7 pgs.

Kunihiro Chibara et al, "A Dual–Probe Blood Flow–Mapping System Using Doppler Ultrasound", IEICE Transactions, Institute of Electronics, Information and Comm. Engineers, Tokyo, Japan, vol. E74, No. 9, Sep. 1, 1991, pp. 2625–2633.

* cited by examiner

PHYSIOLOGICAL OBJECT DISPLAYS

This application claims priority under 35 U.S.C. § 120 and is a continuation-in-part of U.S. Ser. No. 09/706,512, filed on Nov. 3, 2000, now U.S. Pat. No. 6,743,172 and claims priority under 35 U.S.C. § 120 to U.S. Provisional Patent Application Ser. No: 60/263,861, filed on Jan. 23, 2001.

FIELD OF THE INVENTION

This invention relates to display systems for displaying complex medical information to a physician. More specifically, the invention relates to hardware, software and object displays for displaying complex physiological information to physicians in unique graphical display formats in real time.

BACKGROUND OF THE INVENTION

Medical display systems provide information to physicians in a clinical setting. Typical display systems provide data in the form of numbers and one-dimensional signal waveforms that must be assessed, in real time, by the attending physician. Alarms are sometimes included with such systems to warn the physician of an unsafe condition, e.g., a number exceeds a recommended value. In the field of anesthesiology, for example, the anesthesiologist must monitor the patient's condition and at the same time (i) recognize problems, (ii) identify the cause of the problems, and (iii) take corrective action during the administration of the anesthesia. An error in judgment can be fatal.

Physiologic data displays of the patient's condition play a central role in allowing surgeons and anesthesiologists to observe problem states in their patients and deduce the most likely causes of the problem state during surgery, thus allowing expeditious treatment. As one might predict, 63 percent of the reported incidents in the Australian Incident Monitoring Study (AIMS) database were considered detectable with standard data monitors and potentially avoidable. Others have attempted to address these problems, but with only limited success.

For example, Cole, et. al. has developed a set of objects to display the respiratory physiology of intensive care unit (ICU) patients on ventilators. This set of displays integrates information from the patient, the ventilator, rate of breathing, volume of breathing, and percent oxygen inspired. Using information from object displays, ICU physicians made faster and more accurate interpretations of data than when they used alphanumeric displays. Cole published one study that compared how physicians performed data interpretation using tabular data vs. printed graphical data. However, Cole's work did not utilize all of the methods being leveraged in aviation and nuclear power to involve a system for receiving analog data channels and driving real-time graphical displays on a medical monitor.

Ohmeda, a company that makes anesthesia machines, manufacturers the Modulus CD machine which has an option for displaying data in a graphical way. The display has been referred to as a glyph. Physiologic data is mapped onto the shape of a hexagon. Six data channels generate the six sides of the hexagon. Although this display is graphical, the alphanumeric information of the display predominates. There is no obvious rational for why the physiologic data is assigned a side of the hexagon. Moreover, symmetric changes to the different signs of this geometric shape are very hard for individuals to differentiate. Overall, information displays that show the quantitative (data value), qualitative (high, low, normal zones for the parameter), temporal (trending and change over time), and relational (manner in which multiple parameters relate to disease states that need treatment) information that clinicians need in an intuitive manner are lacking.

The physiologic parameters that relate to oxygen transportation are central to medical assessment of any patient's well being. A review of the physiological parameters of interest and their importance in medical decision making that are represented in the informational display of this application, follows:

Blood adequacy: In the surgical and postoperative settings, decisions regarding the need for blood transfusion normally are guided by hemoglobin (Hb) or hematocrit levels (Hct). Hematocrit is typically defined as the percentage by volume of packed red blood cells following centrifugation of a blood sample. If the hemoglobin level per deciliter of blood in the patient is high, the physician can infer that the patient has sufficient capacity to carry oxygen to the tissue. During an operation this value is often used as a trigger; i.e. if the value falls below a certain point, additional blood is given to the patient. While these parameters provide an indication of the arterial oxygen content of the blood, they provide no information on the total amount of oxygen transported (or "offered") to the tissues, or on the oxygen content of blood coming from the tissues.

For example, it has been shown that low postoperative hematocrit may be associated with postoperative ischemia in patients with generalized atherosclerosis. Though a number of researchers have attempted to define a critical Hct level, most authorities would agree that an empirical automatic transfusion trigger, whether based on Hb or Hct, should be avoided and that red cell transfusions should be tailored to the individual patient. The transfusion trigger, therefore, should be activated by the patient's own response to anemia rather than any predetermined value.

Tissue oxygenation: This is, in part, due to the fact that a number of parameters are important in determining how well the patient's tissues are actually oxygenated. In this regard, the patient's cardiac output is also an important factor in correlating hemoglobin levels with tissue oxygenation states. Cardiac output or CO is defined as the volume of blood ejected by the left ventricle of the heart into the aorta per unit of time (ml/min) and can be measured with thermodilution techniques. For example, if a patient has internal bleeding, the concentration of hemoglobin in the blood might be normal, but the total volume of blood will be low. Accordingly, simply measuring the amount of hemoglobin in the blood without measuring other parameters such as cardiac output is not always sufficient for estimating the actual oxygenation state of the patient.

More specifically the oxygenation status of the tissues is reflected by the oxygen supply/demand relationship of those tissues i.e., the relationship of total oxygen transport ($DO_2$) to total oxygen consumption ($VO_2$). Hemoglobin is oxygenated to oxyhemoglobin in the pulmonary capillaries and then carried by the cardiac output to the tissues, where the oxygen is consumed. As oxyhemoglobin releases oxygen to the tissues, the partial pressure of oxygen ($PO_2$) decreases until sufficient oxygen has been released to meet the oxygen consumption ($VO_2$). Although there have been advances in methods of determining the oxygenation status of certain organ beds (e.g., gut tonometry; near infrared spectroscopy) these methods are difficult to apply in the clinical setting. Therefore, the use of parameters that reflect the oxygenation status of the blood coming from the tissues i.e., the partial pressure of oxygen in the mixed venous blood ($PvO_2$; also known as the mixed venous blood oxygen tension) or mixed venous blood oxyhemoglobin saturation ($SvO_2$) has become a generally accepted practice for evaluating the global oxygenation status of the tissues.

Unfortunately, relatively invasive techniques are necessary to provide more accurate tissue oxygenation levels. In this respect, direct measurement of the oxygenation state of a patient's mixed venous blood during surgery may be made using pulmonary artery catheterization. To fully assess whole body oxygen transport and delivery, one catheter (a flow directed pulmonary artery [PA] catheter) is placed in the patient's pulmonary artery and another in a peripheral artery. Blood samples are then drawn from each catheter to determine the pulmonary artery and arterial blood oxygen levels. As previously discussed, cardiac output may also be determined using the PA catheter. The physician then infers how well the patient's tissue is oxygenated directly from the measured oxygen content of the blood samples.

While these procedures have proven to be relatively accurate, they are also extremely invasive. For example, use of devices such as the Swan-Ganz® thermodilution catheter (Baxter International, Santa Ana, Calif.) can lead to an increased risk of infection, pulmonary artery bleeding, pneumothorax and other complications. Further, because of the risk and cost associated with PA catheters, their use in surgical patients is restricted to high-risk or high-blood-loss procedures (e.g., cardiac surgery, liver transplant, radical surgery for malignancies) and high-risk patients (e.g., patients who are elderly, diabetic, or have atherosclerotic disease).

Among other variables, determination of the oxygenation status of the tissues should include assessment of the amount of blood being pumped toward the tissues (CO) and the oxygen content of that (arterial) blood ($CaO_2$). The product of these variables may be used to provide a measure of total oxygen transport ($DO_2$). Currently, assessment of $DO_2$ requires the use of the invasive monitoring equipment described above. Accordingly, determination of $DO_2$ is not possible in the majority of surgical cases. However, in the intensive care unit (ICU), invasive monitoring tends to be a part of the routine management of patients; thus, $DO_2$ determinations are obtained more readily in this population.

Partial pressure of oxygen in the mixed venous blood or mixed venous blood oxygen tension ($PvO_2$) is another important parameter that may be determined using a PA catheter. Because of the equilibrium that exists between the partial pressure of oxygen ($PO_2$) in the venous blood and tissue, a physician can infer the tissue oxygenation state of the patient. More specifically, as arterial blood passes through the tissues, a partial pressure gradient exists between the $PO_2$ of the blood in the arteriole passing through the tissue and the tissue itself. Due to this oxygen pressure gradient, oxygen is released from hemoglobin in the red blood cells and also from solution in the plasma; the released $O_2$ then diffuses into the tissue. The $PO_2$ of the blood issuing from the venous end of the capillary cylinder ($PvO_2$) will generally be a close reflection of the $PO_2$ at the distal (venous) end of the tissue through which the capillary passes.

Closely related to the mixed venous blood oxygen tension ($PvO_2$) is the mixed venous blood oxyhemoglobin saturation ($SvO_2$) which is expressed as the percentage of the available hemoglobin bound to oxygen. Typically, oxyhemoglobin disassociation curves are plotted using $SO_2$ values vs. $PO_2$ values. As the partial pressure of oxygen ($PO_2$) decreases in the blood (i.e. as it goes through a capillary) there is a corresponding decrease in the oxygen saturation of hemoglobin ($SO_2$). While arterial values of $PO_2$ and $SO_2$ are in the neighborhood of 95 mm Hg and 97% respectively, mixed venous oxygen values ($PvO_2$, $SvO_2$) are on the order of 45 mm Hg and 75% respectively. As such $SvO_2$, like $PvO_2$, is indicative of the global tissue oxygenation status. Unfortunately, like $PvO_2$, it is only measurable using relatively invasive measures.

Another rather informative parameter with respect to patient oxygenation is deliverable oxygen ($dDO_2$). $dDO_2$ is the amount of the oxygen transported to the tissues ($DO_2$) that is able to be delivered to the tissues (i.e. consumed by the tissues) before the $PvO_2$ (and by implication the global tissue oxygen tension) falls below a certain value. For instance the $dDO_2(40)$ is the amount of oxygen that can be delivered to the tissues (consumed by the tissues) before $PvO_2$ is 40 mm Hg while $dDO_2(35)$ is the amount consumed before the $PvO_2$ falls to 35 mm Hg.)

Additional relevant parameters may be determined non-invasively. For instance, whole body oxygen consumption ($VO_2$) can be calculated from the difference between inspired and mixed expired oxygen and the minute volume of ventilation. Cardiac output may also be non-invasively inferred by measuring arterial blood pressure instead of relying on thermodilution catheters. For example, Kraiden et al. (U.S. Pat. No. 5,183,051, incorporated herein by reference) use a blood pressure monitor to continuously measure arterial blood pressure. These data are then converted into a pulse contour curve waveform. From this waveform, Kraiden et al. calculate the patient's cardiac output.

Regardless of how individual parameters are obtained, those skilled in the art will appreciate that various well established relationships allow additional parameters to be derived. For instance, the Fick equation (Fick, A. Wurzburg, *Physikalisch edizinische Gesellschaft* Sitzungsbericht 16 (1870)) relates the arterial oxygen concentration, venous oxygen concentration and cardiac output to the total oxygen consumption of a patient and can be written as:

$$(CaO_2 - CvO_2) \times CO = VO_2$$

where $CaO_2$ is the arterial oxygen content, $CvO_2$ is the venous oxygen content, CO is the cardiac output and $VO_2$ represents whole body oxygen consumption.

While the non-invasive derivation of such parameters is helpful in the clinical setting, a more determinative "transfusion trigger" would clearly be beneficial. If $PvO_2$ or $DO_2$ is accepted as a reasonable indicator of patient safety, the question of what constitutes a "safe" level of these parameters arises. Though data exists on critical oxygen delivery levels in animal models, there is little to indicate what a critical $PvO_2$ might be in the clinical situation. The available data indicate that the level is extremely variable. For instance, in patients about to undergo cardiopulmonary bypass, critical $PvO_2$ varied between about 30 mm Hg and 45 mm Hg where the latter value is well within the range of values found in normal, fit patients. Safe $DO_2$ values exhibit similar variability.

For practical purposes a $PvO_2$ value of 35 mm Hg or more may be considered to indicate that overall tissue oxygen supply is adequate, but this is implicit on the assumption of an intact and functioning vasomotor system. Similarly, the accurate determination of $DO_2$ depends on an intact circulatory system. During surgery it is necessary to maintain a wide margin of safety and probably best to pick a transfusion trigger (whether $DO_2$, $PvO_2$, $SvO_2$ or some derivation thereof) at which the patient is obviously in good condition as far as oxygen dynamics are concerned. In practice, only certain patients will be monitored with a pulmonary artery catheter. Accordingly, the above parameters will not be available for all patients leaving the majority to be monitored with the imperfect, and often dangerous, trigger of Hb concentration.

Efforts to resolve these problems in the past have not proven entirely successful. For example, Faithfull et al. (*Oxygen Transport to Tissue XVI*, Ed. M. Hogan, Plenum Press, 1994, pp. 41–49) describe a model to derive the oxygenation status of tissue under various conditions. However, the model is merely a static simulation allowing an operator to gauge what effect changing various cardiovascular or physical parameters will have on tissue oxygenation. No provisions are made for continuous data acquisition and evaluation to provide a dynamic representation of what may actually be occurring. Accordingly, the model cannot be used to provide real-time measurements of a patient's tissue oxygenation under changing clinical conditions.

Just as tissue oxygenation physiology has been reviewed, ventilation (the movement of air and medical gases in and out of the lung) and oxygenation (the loading of red cell hemoglobin with oxygen in the lung) are critical processes that impact on tissue oxygenation. Thus, what is needed in the art are relatively non-invasive systems for intuitively displaying physiological information to a physician. The emodiments system described below provide such a system to improve a physician's interpretation of patient data (in the areas of ventilation, oxygenation and perfusion). Other aspects of the invention will become apparent in the description that follows.

U.S. Pat. No. 6,234,963 is hereby incorporated by reference. *Nunn's Applied Respiratory Physiology*, $4^{th}$ Ed., J. F. Nunn, is also hereby incorporated by reference.

SUMMARY OF THE INVENTION

The present invention relates to systems and methods for obtaining physiological information from patients and displaying that information in an intuitive and logical format to a physician. The intuitive format may be termed a medical process diagram or object display because physicians reading the displayed information can quickly perceive the importance of changing patient values.

Research in applied human factors has focused on using graphical displays in high-risk environments similar to the operating room (e.g., nuclear power control rooms and airplane cockpits and flight decks) to reduce human error. The success of medical process diagrams appears to be a function of how well the operator's cognitive needs are illustrated and mapped into the graphical elements of the display. Using accepted task-analysis methods, a system was developed describing how medical doctors interpret oxygen-transport physiological data to diagnose pathological states and subsequently take appropriate corrective action for their patients. In an effort to make the voluminous data that doctors need to interpret more informative, a set of physiological object displays has been developed.

The object displays of the present invention have been developed to illustrate: 1) the relationships of data to other data; 2) data in context; 3) a frame of reference for the data; 4) the rate of change information for the data; and, 5) event information. Specifically, a system has been developed for presenting and relating cardiac, vascular, hemodynamic, cardiopulmonary, ventilator state, lung airway resistance, oxygenation and oxygen-transport physiology to doctors. The system uses data acquisition hardware, a computer, physiological parameter calculation software and object display software.

Unfortunately, current display systems that present physiologic data to physicians in critical care or other medical settings force the physicians to perform a great deal of cognitive work to interpret that data. Interpreting data in this manner has been shown to be more likely to introduce human error. In contrast, the display systems described below utilize visual memory cues and perceptual diagrams to map complex data graphically and in an intuitive manner for physicians and other medical personnel. These data maps are then displayed to match the mental model physicians use to interpret various physiological parameters. Because the system receives analog signals from the patient and thereafter calculates several physiological quantities, patient data is used to drive the display in real-time.

DETAILED DESCRIPTION OF THE INVENTION

I. Hardware System

Figure 17:
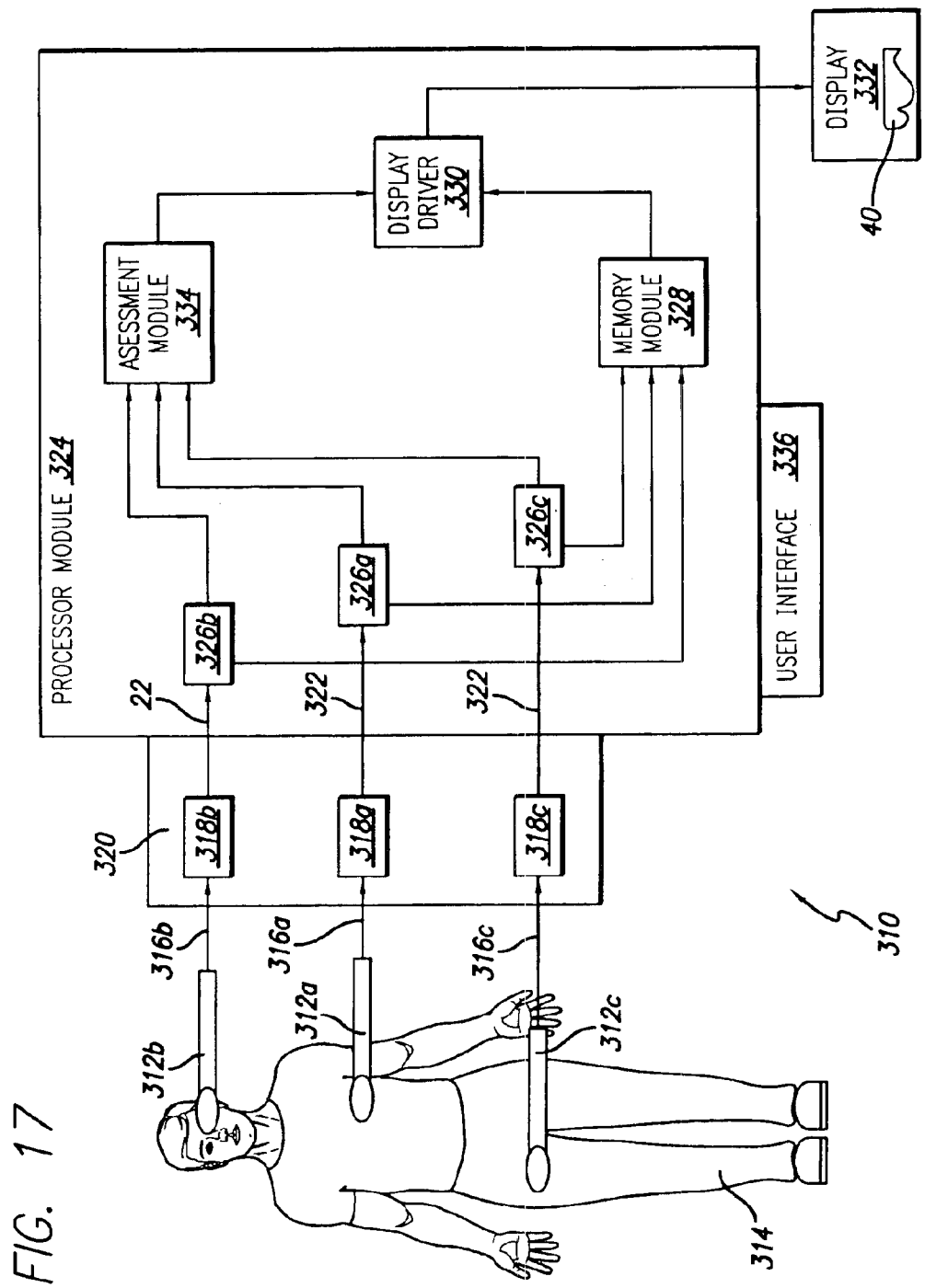
FIG. 17 is a schematic diagram illustrating one system for collecting, processing and displaying various physiological parameters.

FIG. 17 illustrates a system 310 constructed according to an embodiment of the invention. A series of probes 312 are connected to various monitoring activities associated with the patient 314, e.g., a heart rate probe 12a. These probes are well known and typically generate analog signals 316 representative of the monitored activity. The signals 316 are converted through well-known A/D devices 318 in a data conversion module 320 to generate digital data corresponding to the analog signals 16. This data is made available on a data bus 322.

A processing module 324 processes data on the bus 322 to generate usable quantitative measures of patient activity as well as to compare and create object displays that, for example: (1) relate certain data relative to other data; (2) present data in context; (3) relate data to a frame of reference; (4) determine the rate of change information in the data; and/or (5) to present event information.

One embodiment of the module 324 thus includes a plurality of data processing sections 326a–326c that analyze and/or quantify the data being input from the probe 312. For example, one section 326a, connected in the data chain to probe 312a, processes data on the bus 322 to provide a representation of heart rate in the form of a digital word. As the patient's heart rate changes, so does the digital word. A memory module 328 is used to store selected data, such as the digital word corresponding to heart rate, so that the module 324 contains a record and a current value of the patient's heart rate activity. The memory 328 also stores information, such as nominal values from which to compare data to a frame of reference, or such as extreme values representative of desired patient thresholds. The display driver section 330, connected to sections 326a–326c, can thus command the display of the heart rate data in context on the display 332, and/or relative to frame of reference data within the memory 328.

The data from the sections 326a–326c can also be compared to other data or related to stored thresholds within the assessment module 334. By way of example, data corresponding to probe 312a can be compared relative to probe 312b through a process of digital division within the module 334. The driver 330 can in turn command the display of this related data on the display 332. In another example, the assessment module 334 can compare other data to stored data within the memory 328; and a warning event can be displayed on the display 332 if the comparison exceeds a set threshold.

Those skilled in the pertinent technology should appreciate that certain probes 312 may have self-contained A/D conversion capability and data manipulation. Furthermore, such probes can easily be connected directly to the assessment module 334 and memory 328 by known techniques.

The system 310 is controlled by inputs at a user interface 336, such as a keyboard, and the display driver 330 formats data into various object formats on the display 332. Accordingly, by commanding selected processes within the assessment module 334—such as comparison of certain data with other data—such data can be automatically displayed on the display 332 in the desired object format. The particular object displays, according to the invention, are described below. These object displays can be displayed simultaneously on different or the same display and thus sufficient probes are required to collect the associated data.

Figure 18:
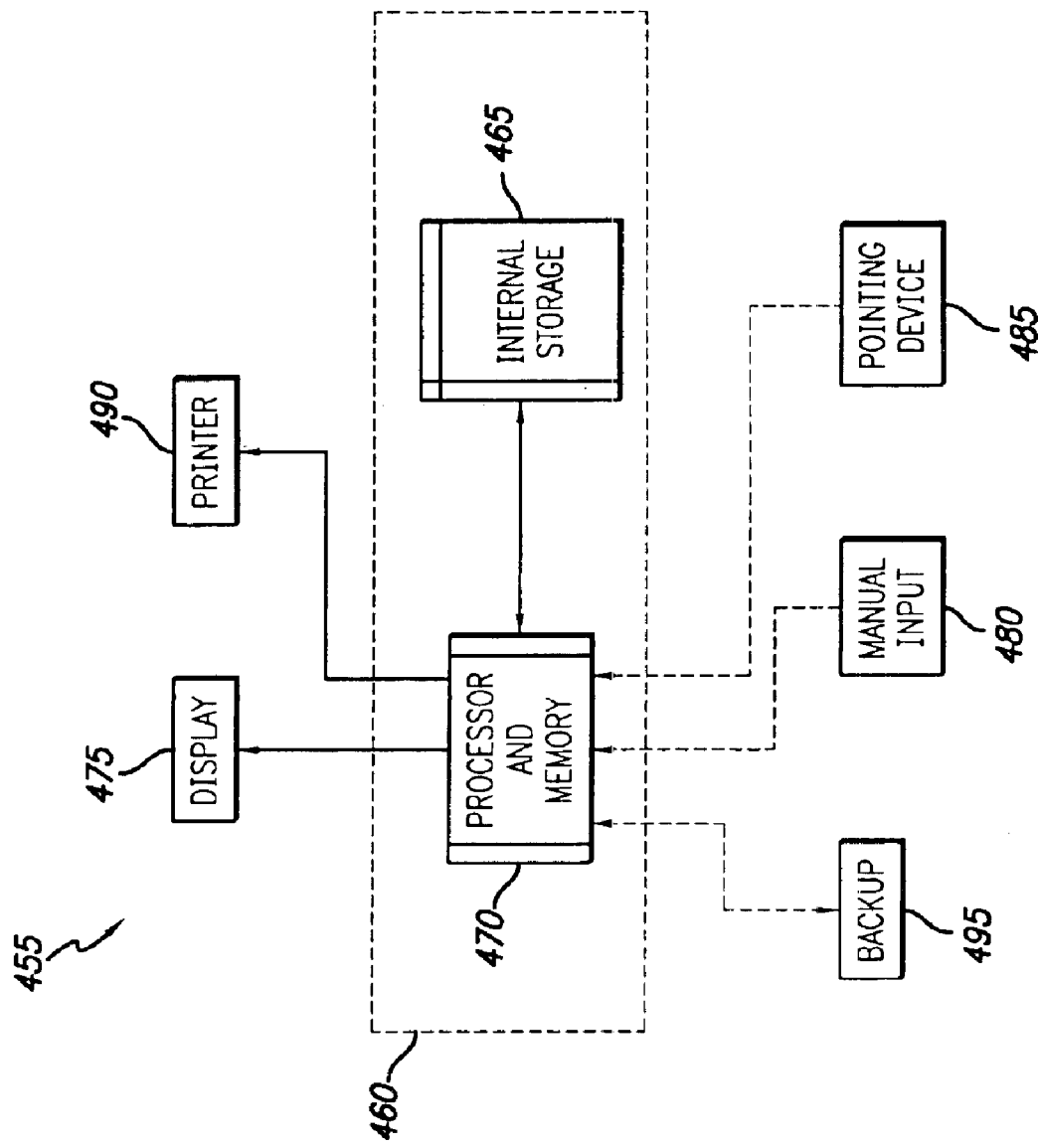
FIG. 18 is a schematic diagram of one embodiment that can be used to run the present system; and, FIG. 19 is a flowchart detailing a software scheme that may be used to run the present invention.

FIG. 18 shows a representative computer system 455 that may be used in conjunction with the system 310 of FIG. 17. System 455 can be operated in a stand-alone configuration or as part of a network of computer systems. The system 455 can be an integrated system that collects data from the patient and presents processed data to a display for viewing by a physician or other medical personnel.

The computer system 455 includes various software executed in conjunction with an operating system, for instance any of the Windows software available from the MICROSOFT Corporation, on a computer 460. Other embodiments may use a different operational environment or a different computer or both.

In an alternate embodiment of the invention, computer 460 can be connected via a wide area network (WAN) connection to other physicians or hospitals. A WAN connection to other medical institutions enables a real-time review of the patient's progress during surgery or in the intensive care unit.

Referring again to FIG. 18, one embodiment of the computer 460 includes an Intel Pentium or similar microprocessor running at 128 MHz and 128 Kilobytes (Kb) of RAM memory (not shown). The system 455 includes a storage device 465, such as a hard disk drive connected to the processor 470. The hard drive 465 is optional in a network configuration, i.e., the workstation uses a hard disk or other storage device in a file server. If the computer 460 is used in the stand-alone configuration, the hard drive 465 is preferably 2.0 Gb or more. However, the system is not limited to particular types of computer equipment. Any computer equipment that can run the display system described herein is anticipated to function within the scope of this invention.

The computer 460 is integrated with a group of computer peripherals, and is connected to a VGA (video graphics array) display standard, or a color video monitor, which provides the display output of the system 455. The display 475 may be a 15, 17 or 19 inch monitor running at (1024× 768) pixels with (65,536) colors. A keyboard 480 that is compatible with IBM AT type computers may be connected to the computer 460. A pointing device 485, such as a two or three button mouse can also connect to the computer 460. Reference to use of the mouse is not meant to preclude use of another type of pointing device.

A printer 490 may be connected to provide a way to produce hard-copy output, such as printouts for file records. In one configuration, a backup device 495, such as a Jumbo (2 Gb) cartridge tape back-up unit, available from Colorado Memory Systems, is preferably connected to the computer 460.

In an alternate embodiment of a stand-alone configuration, or as one of the workstations of a network configuration, the system 455 may include a portable computer, such as a laptop or notebook computer or other computers available from a variety of vendors. The portable computer (not shown) is equipped with components similar to that described in conjunction with computer 460.

It will be understood by one skilled in the technology that a programmed computer can also be implemented completely or partially with custom circuitry. Therefore, the chosen implementation should not be considered restrictive in any matter.

II. Software

Many different ways of implementing the software of the present invention will be known to skilled technologists. For example, programming languages such as (Labview, C++, Basic, Cobol, Fortran or Modula-2) can be used to integrate the features of the present invention into one software package. An alternative method of illustrating the software of the present invention is to use a spreadsheet program to collect and determine the $PvO_2$ or other data of a patient in real-time. This method is described in detail below.

As discussed above, the systems and methods of the present invention collect data from a patient and determine various physiological parameters of a patient in real-time. Software is used to direct this process. Those skilled in the art will appreciate that the desired parameters may be derived and displayed using various software structures written in any one of a number of languages.

Figure 19:
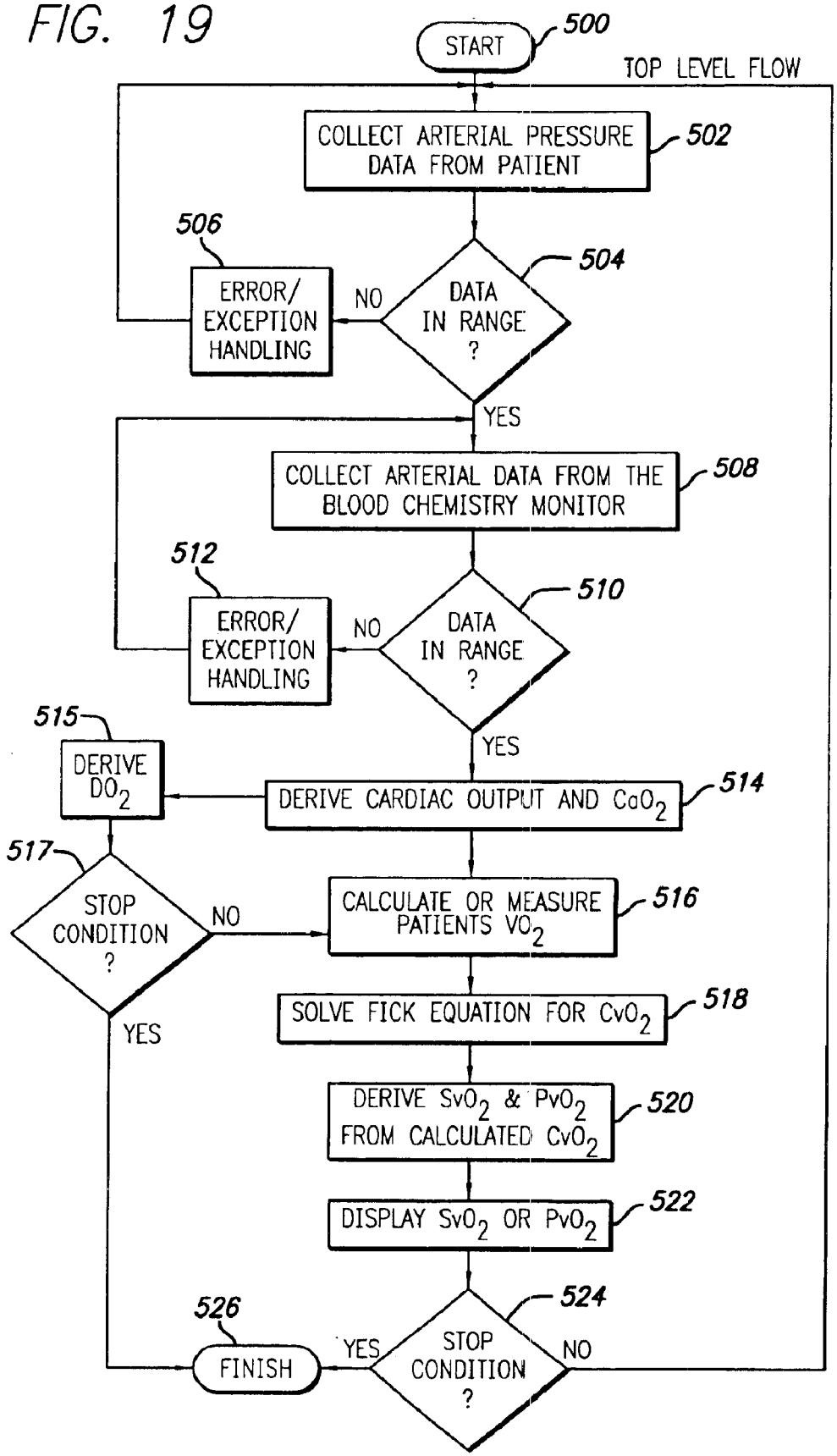

Referring now to FIG. 19, the process is begun when a start signal is transmitted by the user to the system at start state 500. The start signal can be a keystroke of mouse command that initiates the software to begin collecting data. After receiving the start command at state 500, arterial pressure data is collected from a patient at state 502. Arterial pressure data may be collected by hooking a patient up to an arterial pressure monitor as is well known.

Once data have been collected from a patient at state 502, a "data in range" decision is made at decision state 504. At this stage, the software compares the data collected at state 502 with known appropriate ranges for arterial pressure values. Appropriate ranges for arterial pressure data are, for example, between 70/40 and 250/140.

If data collected at process state 502 are not within the range programmed in decision state 504, or if the arterial pressure wave is abnormal, an error/exception handling routine is begun at state 506. The error handling routine at state 506 loops the software back to process state 502 to re-collect the arterial pressure data. In this manner, false arterial pressure data readings will not be passed to the rest of the program. If the data collected at process state 502 are in the appropriate range at decision state 504, the software pointer moves to process state 508 that contains instructions for collecting arterial data. Preferably the collected data will include patient temperature, arterial pH, hemoglobin levels, $PaO_2$ and $PaCO_2$. Moreover, the data is preferably generated by an attached blood chemistry monitor which may provide information on the patient's blood gas levels, acid-base status and hematology status. In such embodiments the data is collected by receiving data streams via the serial connection from the blood chemistry monitor into the computer. Alternatively, the relevant values may be obtained from accessing data that is manually input from the keyboard.

As described previously, the blood chemistry monitor continually samples arterial blood from the patient preferably determining several properties of the patient's blood from each sample. Data corresponding to each of the properties taken from the blood chemistry monitor at process state 508 are checked so that they are in range at decision state 510. An appropriate range for the pH is 7.15 to 7.65. An appropriate range for the hemoglobin level is from 0 to 16 g/dL. An appropriate range for the $PaO_2$ is from 50 mm Hg to 650 mm Hg while an appropriate range for the $PCO_2$ is from 15 mm Hg to 75 mm Hg.

If data are not within the appropriate ranges for each specific variable at decision state 510, an error/exception handling routine at state 512 is begun. The error/exception handling routine at state 512 independently analyzes variables collected at state 508 to determine whether it is in range. If selected variables collected at state 508 are not within the appropriate range, the error/exception handling routine 512 loops a software pointer back to state 508 so that accurate data can be collected. If the selected data are in range at decision box 510, the software then derives the $CaO_2$ value along with the cardiac output (CO) from the previously obtained arterial pressure data at state 514.

As discussed, cardiac output can be derived from arterial pressure measurements by any number of methods. For example, the Modelflow system from TNO Biomedical can derive a cardiac output value in real-time from an arterial pressure signal. Other methods, as discussed above, could also be used at process step 514 to determine cardiac output. Once a cardiac output value has been determined at process step 514, the patient's total oxygen transport ($DO_2$) may be derived at process step 515. As previously discussed the total oxygen transport is the product of the cardiac output and the arterial blood oxygen content. This parameter may optionally be displayed and, as indicated by decision state 517, the program terminated if the software has received a stop command. However, if the software has not received a keyboard or mouse input to stop collecting data at decision state 517, a pointer directs the program to process state 516 to derive further parameters. Specifically, process state 516 relates to the measurement or input of the patient's $VO_2$.

The patient's $VO_2$ can be calculated using the methods previously described measured by hooking the patient up to a suitable ventilator and measuring his oxygen uptake through a system such as the Physioflex discussed above or using a number of other devices such as systems manufactured by Sensormedics and Puritan Bennett. By determining the amount of oxygen inspired and expired, the ventilator may be used to calculate the total amount of oxygen absorbed by the patient. After the patient's $VO_2$ value has been determined at process step 516, these variables are applied to the Fick equation at state 518 to provide a real time $CvO_2$. The Fick equation is provided above.

Once the $CvO_2$ is known, mixed venous oxyhemoglobin saturation ($SvO_2$) and the mixed venous oxygen tension ($PvO_2$) can be derived at state 520. As previously explained, values for mixed venous pH and $PCO_2$ are assumed to have a constant (but alterable) relation to arterial pH and $PaCO_2$ respectively and these are used, along with other variables, in the Kelman equations to define the position of the oxyhemoglobin dissociation curve. Alternatively, algorithms can be derived to calculate these values. Knowing the Hb concentration, a $PvO_2$ is derived that then provides a total $CvO_2$ (which includes contributions from Hb, plasma and PFC) equal to the $CvO_2$ determined from the Fick equation. If the $CvO_2$ value will not "fit" the Fick equation, another $PvO_2$ value is chosen. This process is repeated until the Fick equation balances and the true $PvO_2$ is known.

Those skilled in the art will appreciate that the same equations and algorithms may be used to derive, and optionally display, the mixed venous blood oxyhemoglobin saturation $SvO_2$. That is, $SvO_2$ is closely related to $PvO_2$ and may easily be derived from the oxygen-hemoglobin dissociation curve using conventional techniques. It will further be appreciated that, as with $PvO_2$, $SvO_2$ may be used to monitor the patient's oxygenation state and as an intervention trigger if so desired by the clinician. As discussed above, mixed venous blood oxyhemoglobin saturation may be used alone in this capacity or, more preferably, in concert with the other derived parameters.

After deriving values for $PvO_2$, $SvO_2$ or both, the value or values may be displayed on the computer display at step 522. If the software has not received a keyboard or mouse input to stop collecting data at decision state 524, a pointer loops the program back to process state 502 to begin collecting arterial pressure data again. In this manner, a real-time data loop continues so that the patient's mixed venous blood oxygen tension ($PvO_2$) or saturation ($SvO_2$) is constantly updated and displayed on the computer at state 522. If the software has received a stop command from a keyboard or mouse input at decision state 524, then a finish routine 526 is begun.

III. Calculating Physiological Values

The following system can utilize a large Microsoft EXCEL® spreadsheet to collect information from the patient and display the desired physiological parameters. Before receiving real-time inputs of cardiovascular and oxygenation variables, a number of oxygenation constants may be entered into the system. These constants preferably include the patient's estimated blood volume, oxygen solubility in plasma and the oxygen content of 1 g of saturated oxyhemoglobin. The oxygenation constants are then stored in the computer's memory for use in later calculations.

TABLE 1 shows commands from part of a Microsoft EXCEL® spreadsheet that collects a patient's data and derives the value of the desired oxygenation parameters. The program is initialized by assigning names to various oxygenation constants that are to be used throughout the software. In the embodiment shown, oxygenation constants corresponding to blood volume (BV), oxygen solubility in a perfluorocarbon emulsion (O2SOL), specific gravity of any perfluorocarbon emulsion (SGPFOB), intravascular half-life of a perfluorocarbon emulsion (HL), weight/volume of a perfluorocarbon emulsion (CONC), barometric pressure at sea level (BARO), milliliters oxygen per gram of saturated hemoglobin (HbO) and milliliters of oxygen per 100 ml plasma per 100 mm of mercury (PIO) are all entered. The constants relating to perfluorocarbons would be entered in the event that fluorocarbon blood substitutes were going to be administered to the patient.

An example of starting values for Kelman constants, a subset of the oxygenation constants, is also shown in TABLE 1. These starting values are used in later calculations to derive the patient's mixed venous oxygenation state or other desired parameters such as mixed venous blood oxyhemoglobin saturation. As with the other oxygenation constants the Kelman constants are also assigned names as shown in TABLE 1.

After the oxygenation constants, including the Kelman constants, have been assigned names, real time inputs from the arterial pressure lines and blood chemistry monitor may be initialized and begin providing data. As shown in TABLE 2, the system depicted in this embodiment derives or receives data relating to the arterial oxyhemoglobin saturation percentage ($SaO_2$). In particular, saturation percentages are derived from arterial data for oxygen tension ($PaO_2$), pH (pHa), carbon dioxide tension ($PaCO_2$) and body temperature (TEMP). If desired by the clinician, the present invention provides for the real-time display of $SvO_2$ values (as derived from calculated $PvO_2$, pHv, $PvCO_2$ and temperature) to be used for the monitoring of the patient's tissue oxygenation status. As previously discussed, values for $PvCO_2$ and pHv are related, by a fixed amount, to those of $PaCO_2$ and pHa respectively as determined by algorithms. Cardiac output (CO) is also input as is $VO_2$.

When Hb concentration, arterial blood gas and acid/base parameters are entered (automatically or manually) into the program, the $O_2$ delivery and consumption variables for both red cell containing Hb and for the plasma phase may be determined. Those variables relating to PFC (in the case of blood substitutes) or Hb based oxygen carrier can also be determined.

Numerical values useful for the calculation of $CaO_2$ relate to Hb concentration, arterial oxygen tension ($PaO_2$), arterial carbon dioxide tension ($PaCO_2$), arterial pH (pHa) and body temperature. The position of the oxygen-hemoglobin dissociation curve is calculated using the Kelman equations, which are input as oxygenation constants in the program. These calculations produce a curve that, over the physiological range of $O_2$ tensions, is indistinguishable from the parent curve proposed by Severinghaus (*J. Appl. Physiol.* 1966, 21: 1108–1116) incorporated herein by reference. Iteration may be used to calculate a $PvO_2$ (via $SvO_2$) that results in the required mixed venous oxygen contents in Hb, plasma and fluorocarbon to satisfy the Fick equation.

TABLE 1

| | VALUES AT START: |
|---|---|
| ASSUMPTIONS: | |
| Blood Volume (ml/kg) -BV | 70 |
| $O_2$ solubility in PFB (ml/dl @37 deg C.) -O2SOL | 52.7 |
| Specific Gravity of PFOB -SGPFOB | 1.92 |
| Intravascular half-life of Oxygent HT (hours) -HL = | ½ Life of Oxygent |
| Wgt/Vol of PFOB emulsion/100 -CONC | 0.6 |
| Barometric Pressure @ sea level -BARO | 760 |
| MI O2 per gram saturated Hb -HbO | 1.34 |
| MI O2 per 100 ml plasma per 100 mm Hg -HIO | 0.3 |
| KELMAN CONSTANTS: | |
| Ka1 = | −8.5322289*1000 |
| Ka2 = | 2.121401*1000 |
| Ka3 = | −6.7073989*10 |
| Ka4 = | 9.3596087*100000 |
| Ka5 = | −3.1346258*10000 |
| Ka6 = | 2.3961674*1000 |
| Ka7 | −67.104406 |

TABLE 2

| INPUTS: | AT START: |
|---|---|
| Hemoglobin (Gm/dl) -Hb | 6 |
| Arterial Oxyhemoglobin saturation (%) -SaO2 | |
| Calculated Arterial Oxyhemoglobin saturation (%) - = SaO2CALC | 100*(SPaO2*(SPaO2*(SPaO2*(SPaO2 + Ka3) + Ka2) + Ka1))/(SPaO2*(S |
| Active Input Value for SaO2 -SaO2USED = | IF(SaO2 <> O, SaO2, SaO2CALC) |
| Mixed venous blood oxyhemoglobin saturation (%) -SvO2 | |
| Calculated Mixed venous blood oxyhemoglobin saturation = -SVO2CALC | 100*(SPvO2*(SPvO2*(SPvO2*(SPvO2 + Ka3) + Ka2) + Ka1))/SPvO2*(SP |
| Active Input Value for SvO2 -SvO2USED = | IF(SvO2 <> O, SvO2, SvO2CALC) |
| Arterial Oxygen Partial Pressure (mm Hg) -PaO2 | 100 |
| Calculated 'standardized' PaO2 -SPaO2 = | PaO2*10^((0.024*(37-TEMPUSED)) + (0.4*(pHaUSED-7.4)) + (0.06*(LOG10(40)- |
| Active Input Value for PaSO2 -PaSO2USED = | IF(PaO2 <> O, PaO2, SPaO2) |
| Arterial pH -pHa | |
| Normal Arterial pH -pHaNORM | 7.4 |
| Active Input Arterial pH -pHaUSED = | IF(pHa <> O, pHa, pHaNORM) |
| Arterial PCO2 -PaCO2 | |
| Normal PaCO2 -PaCO2NORM | 40 |
| Active Input Arterial PCO2 -PaCO2USED = | IF(PaCO2 <> O, PaCO2, PaCO2NORM) |
| Body Temp C. -TEMP | |
| Normal Body Temp C. -TEMPNORM | 37 |
| Active Input Body Temp C. -TEMPUSED = | IF(TEMP <> O, TEMP, TEMPNORM) |
| Mixed Venous Oxygen Partial Pressure (mm Hg) -PvO2 | 40.6819722973629 |
| Calculated 'standardized' PvO2 -SPvO2 = | PvO2*10^((0.024*(37-TEMPUSED)) + (0.4*(pHvUSED-7.4)) + (0.06*(LOG10(40)- |
| Mixed Venous pH -pHv | |
| Normal Venous pH | 7.4 |
| Active Input Mixed Venous pH -pHvUSED = | IF(pHv <> O, pHv, pHvNORM) |
| Mixed Venous PCO2 -PvCO2 | |
| Normal Mixed Venous PCO2 -PvCO2NORM | 40 |
| Active Input Mixed Venous PCO2 -PvCO2USED = | IF(PvCO2 <> O, PvCO2, PvCO2NORM) |
| Cardiac Output (l/mm) -CO = | ((14 - Hemoglobin (gm/dl) * CO Response to 1 gram of Hb Depletion) + 5 |
| CO Response to 1 gr Hb depletion -COCHG | 0.7 |
| Intravascular Oxygent HT Dose(ml/kg) -PFB | |
| Time Adj. Intravascular Oxygent HT Conc(ml/kg) -TAPFB | |
| Patient's Weight (kg) -kg | 70 |
| Total O2 Consumption (ml/min/kg) -VO2KG | 3 |
| Calculated Blood Volume (ml) -CBV = | BV*kg |
| Calc input Total O2 Consumption (ml/min/kg) -VO2 = | kg*VO2KG |

TABLE 3

| DESCRIPTION: | CALCULATIONS: |
|---|---|
| Arterial O2 Content in Hemoglobin (ml/dl) -CaO2Hb = | ((Hb*HbO*SaO2USED)/100) |
| Arterial O2 Content in Plasma (ml/dl) -CaO2Pl = | ((PaO2*PlO)/100) |
| Arterial O2 Content in PFB (ml/dl) -CaO2PFB = | ((PFB*kg*CONC)/SGPFOB)/(kg*BV*0.01)*((O2SOL*PaO2)/(100*BARO) |
| Arterial Oxygen Content (ml/dl) -CaO2 = | (CaO2Hb + CaO2Pl + CaO2PFB) |
| Mixed Venous O2 Content in Hemoglobin (ml/dl) -CvO2Hb = | ((Hb*HbO*SvO2USED)/100) |
| Mixed Venous O2 Content in Plasma (ml/dl) -CvO2Pl = | ((PvO2*PlO)/100) |
| Mixed Venous O2 Content in PFB (ml/dl) -CvO2PFB = | ((PFB*kg*CONC)/SGPFOB)/(kg*BV*0.01)*((O2SOL*PvO2)/(100*BARO) |
| Mixed Venous Oxygen Content (ml/dl) -CvO2SUM = | (CvO2Hb + CvO2Pl + CvO2PFB) |
| Mixed Venous Oxygen Content (ml/dl) -CvO2 = | IF(CVO2SUM > O, (CvO2SUM), CVO2CALC2) |
| Mixed Venous O2 Content (ml/dl) -CvO2CALC2 = | CaO2-(VO2/(CO*10)) |
| Percent of VO2 provided from plasma = | ($O_2$ Used From Plasma / Active Input Total $O_2$ Consumption) * 100 |
| Percent VO2 provided by PFB = | 100 * ($O_2$ Used From Perflubron / Active Input Total $O_2$ Consumption) |
| Percent of VO2 provided by plasma and PFB = | 100 * (($O_2$ Used From Plasma + $O_2$ Used From Perflubron / Active Input* |

TABLE 4

| DESCRIPTION: | OUTPUTS: |
|---|---|
| Total Oxygen Transport (ml/min) -TDO2 = | CaO2*CO*10 |
| O2 Transport in Hemoglobin (ml/min) -DO2Hb = | (CaO2Hb)*CO*10 |
| O2 Transport in plasma (ml/min) -DO2Pl = | CaO2Pl*CO*10 |
| O2 Transport in Perflubron (ml/min) -DO2PFB = | CaO2PFB*CO*10 |
| Calc Total O2 Consumption (ml/min) -VO2CALC = | (CaO2-CvO2)*CO*10 |
| Active Input Total O2 Consumption (ml/min) -VO2USED = | IF(VO2 <> O, VO2, VO2CALC) |
| Oxygen Used from Hemoglobin (ml/min) -VO2Hb = | (CaO2Hb-CvO2Hb)*CO*10 |
| Oxygen Used from Plasma (ml/min) -VO2Pl = | (CaO2Pl-CvO2Pl)*(CO*10) |
| Oxygen Used from Perflubron (ml/min) -VO2PFB = | (CaO2PFB-CvO2PFB)*(CO*10) |
| Total Oxygen Extraction Coefficient -OEC = | (CaO2-CvO2)/CaO2 |
| Hemoglobin Oxygen Extraction Coefficient -HOEC = | (SaO2USED-SvO2USED)/SaO2USED |

Based on the numerical values provided, the program calculates oxygenation parameters such as $PvO_2$ and $SvO_2$ in real time, as shown in TABLE 2. These values are then fed into the display system described below to generate perceptual diagrams. These diagrams are then used by the physician to determine, for example, when to alter the patient's clinical management.

TABLE 3 and TABLE 4 show additional information that may be provided by the instant invention further demonstrating its utility and adaptability. More specifically, TABLE 3 provides various oxygenation values that may be calculated using the methods disclosed herein while TABLE 4 provides other indices of oxygen consumption and oxygen delivery that are useful in optimizing patient treatment.

A closer examination of TABLE 3 shows that the system of the present invention may be used to provide the individual oxygen content of different constituents in a mixed oxygen carrying system. In particular, TABLE 3 provides calculations that give the arterial or venous oxygen content of circulating hemoglobin, plasma or blood substitute respectively.

TABLE 4 illustrates that the present invention may also be used to provide real-time information regarding oxygen consumption and delivery. As mentioned previously, Hb or Hct measurements are not a suitable reflection of tissue oxygenation. This is mainly because they only give an indication of the potential arterial $O_2$ content ($CaO_2$), without providing information about the total oxygen transport ($DO_2$) to the tissues where it is to be used. However as seen in TABLE 4 the instant invention solves this problem by providing on line oxygen transport information which is derived based on $CaO_2$ and cardiac output (CO).

Currently cardiac output is measured using thermodilution, and $CaO_2$ is calculated typically by measuring the arterial oxyhemoglobin saturation ($SaO_2$) and hemoglobin levels, and inserting these values into the following equation: $CaO_2=([Hb]\times 1.34\times SaO_2)+(PaO_2\times 0.003)$, where [Hb]=hemoglobin concentration (in g/dL); 1.34=the amount of oxygen carried per gram of fully saturated hemoglobin; $PaO_2$=the arterial oxygen tension; and 0.003 is the amount of oxygen carried by the plasma (per deciliter per mm Hg of oxygen tension).

The present invention combines the continuous cardiac output algorithm with the Kelman equations to provide the position of the oxygen hemoglobin dissociation curve. Using on-line and off-line inputs of body temperature, hemoglobin, and arterial blood gases, the present invention is able to trend $DO_2$ on a continuous basis. The factors used to determine $DO_2$ are displayed along with their product; thus, the etiology of a decrease in $DO_2$ (inadequate cardiac output, anemia, or hypoxia) would be readily apparent to the physician, decisions regarding the appropriate interventions could be made expeditiously, and the results of treatment would be evident and easily followed.

More particularly, preferred embodiments of the invention are used to provide and display real-time $DO_2$, arterial blood gases, hemoglobin concentration and CO (and all other hemodynamic data already discussed such as BP, heart rate, systemic vascular resistance, rate pressure product and cardiac work). As shown in TABLE 3, such embodiments can also provide separate readouts of contributions of Hb, plasma and PFC (if in circulation) to $DO_2$. That is, the oxygen contributions of each component may be accurately monitored and adjusted throughout any therapeutic regimen. Such data would be particularly useful in both the OR and ICU for providing a safety cushion with respect to the oxygenation of the patient.

The importance of maximizing $DO_2$ for certain patients in the ICU has been underscored by recent studies. The present invention may also be used for determining when such intervention is indicated and to provide the data necessary for achieving the desired results. Once $DO_2$ is known it is possible to calculate the maximum $O_2$ consumption ($VO_2$) that could be supported for a certain chosen (and alterable) $PvO_2$. As previously discussed, this value may be termed deliverable oxygen ($dDO_2$). For instance, a $PvO_2$ of 36 mm Hg might be chosen for a healthy 25 year old patient, where as a $PvO_2$ of 42 mm Hg or higher might be needed for an older patient with widespread arteriosclerosis or evidence of coronary atheroma or myocardial ischemia. Oxygen consumption under anesthesia is variable, but almost always lies in the range of 1.5 to 2.5 ml/kg/min. If the supportable $VO_2$, at the chosen $PvO_2$, was well above this range all would be well and no intervention would be necessary. The closer the supportable $VO_2$ to the normal $VO_2$ range the earlier intervention could be considered.

This relationship could be used to provide a single value, based on deliverable oxygen ($dDO_2$) vs. oxygen consumption ($VO_2$), that would simplify patient care. As previously explained, $dDO_2$ is the amount of oxygen transported to the tissue that is able to be delivered before the partial venous oxygen pressure ($PvO_2$) and, by implication, tissue oxygenation tension falls below a defined level. Thus, if it is desired that the $PvO_2$ value not fall below 40 (this number is variable for different patients depending on their general medical condition) then $DO_2$ (and by implication $dDO_2$) must be maintained at sufficient levels.

The supply/demand ratio ($dDO_2/VO_2$) for a selected $PvO_2$ can be used to provide a single value showing that the amount of oxygen being administered is sufficient to maintain the desired oxygenation state. For example, if it is known that the $dDO_2$ required to maintain a $PVO_2$ of 40 is, say, 300 ml/min and the measured ($VO_2$) is 200 ml/min then the patient is being supplied with enough oxygen for his needs. That is, the supply/demand ratio is 300 ml/min÷200 ml/min or 1.5. A supply/demand ratio of 1 would imply that the $PvO_2$ (or other selected parameter i.e. $SvO_2$) was at the selected trigger value (here 40 mm Hg). Conversely, if the $dDO_2$ (deliverable oxygen) is 200 ml/min and the $VO_2$ (oxygen consumption) is 300 ml/min then the ratio is 0.66 and the patient is not receiving sufficient oxygen (i.e., the $PvO_2$ will be less than 40). Continuous monitoring and display of this ratio will allow the clinician to observe the value approaching unity and intervene appropriately.

A. Ventilator Data

Data concerning ventilator state information can be derived from most standard ventilators. For example, many ventilators have a standard RS232 serial port, where most data can be collected in either digital or analog form which can then be used to create the ventilator object displays which would display this information in a more intuitive manner. In other embodiments, ventilator's displays could include information, collected from arterial line sensors, concerning blood gases, pH, hemoglobin values and hemodynamic information such as heart rate, blood pressure, cardiac output and SVR. This data could be integrated with the patient's airway pressure and various compliance data and the system could be integrated to recommend tidal volume, PEEP, RR settings and $FiO_2$ adjustments to a desired oxygenation/ventilation target based upon this information. In the alternative, the ventilator could be peripherally managed by a computer system and act as a gateway for the distribution to computer information systems ("CIS") and/or hospital information system ("HIS") systems.

|  |  | cmH$_2$O | | |
|---|---|---|---|---|
| Ventilator Inputs: |  | Low | High | Max |
| 1. PAP: | peak airway pressure | 15 | 60 | 120 |
| 2. P$_L$P: | plateau pressure | 15 |  | 120 |
| 3. MAP: | mean airway pressure | 15 |  | 120 |
| 4. PEEP: | positive end expiratory pressure | 0 | 30 | 100 |
| 5. RR: | respiratory rate/breathing frequency | 5 |  | 150 (min) |
| 6. I:E: | inspiratory to expiratory (time ratio) |  |  |  |
|  | (I time %) | 10 |  | 80 |
|  | (pause time %) | 0 |  | 30 |
| 7. TV$_I$: | tidal volume inspiration | 0 |  | 2000 ml |
| 8. TV$_E$: | tidal volume expiration | 0 |  | 2000 ml |
| 9. MV$_D$: | minute ventilation delivered | 0 |  | 20 l/min |
| 10. MV$_E$: | minute ventilation expired |  |  |  |
| 11. ETCO$_2$: | end tidal CO$_2$ | 10 |  | 80 |
| 12. FiO$_2$: | fraction inspired oxygen | 21 |  | 100% |
| 13. Pa O$_2$: | partial pressure oxygen |  |  |  |
| 14. C: | compliance |  |  |  |
| 15. EEF: | end expiratory flow |  |  |  |

IV. Object Displays

As discussed above, the computer system 455 of FIG. 18 includes software and systems for displaying medical process diagrams relating the values derived or calculated above. The display system collects physiological values and creates object displays that are presented to the physician or other medical personnel. Although some of the data may be derived by reading raw analog or digital data from a patient monitor or other device, some of the values may be read from calculated data such as shown in TABLES 1–4 above. The system might sample the data at 300 times per second, and update the display every 1 to 2 seconds. However, the system may be capable of higher sampling and display updates to provide the most up to date and accurate data.

As discussed above, the perceptual diagrams comprise a series of data objects representing physiological processes in the body. Examples of these data objects include an extended heart object, vascular circuit objects, cardiopulmonary bypass objects, ventilator state objects, mixed ventilator/lung objects and oxygenation objects. These objects, as discussed below, can be displayed alone or together to provide a perceptual diagram.

Figure 1:
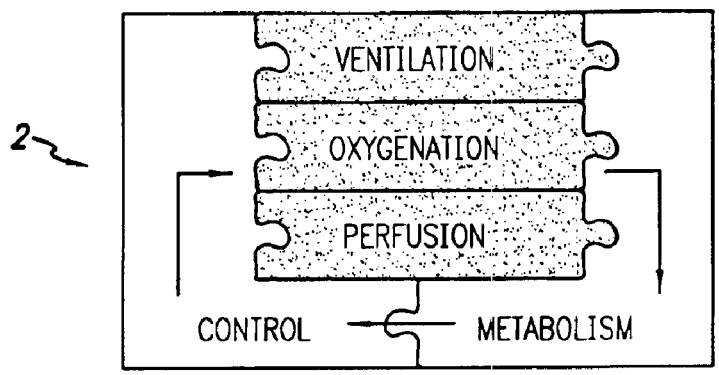
FIG. 1 shows an overview of the oxygen cycle.

FIG. 1 represents a conceptual overview 2 of the inter-relationship of various factors of the oxygen cycle. FIG. 1 demonstrates that ventilation, oxygenation and perfusion interrelate with the control (brain) and metabolism. The various factors are all interconnected and each factor influences the other factors. FIG. 1 demonstrates that metabolism and control each affect one another and both metabolism and control affect ventilation, oxygenation and perfusion.

A. Extended Heart Object

Figure 2:
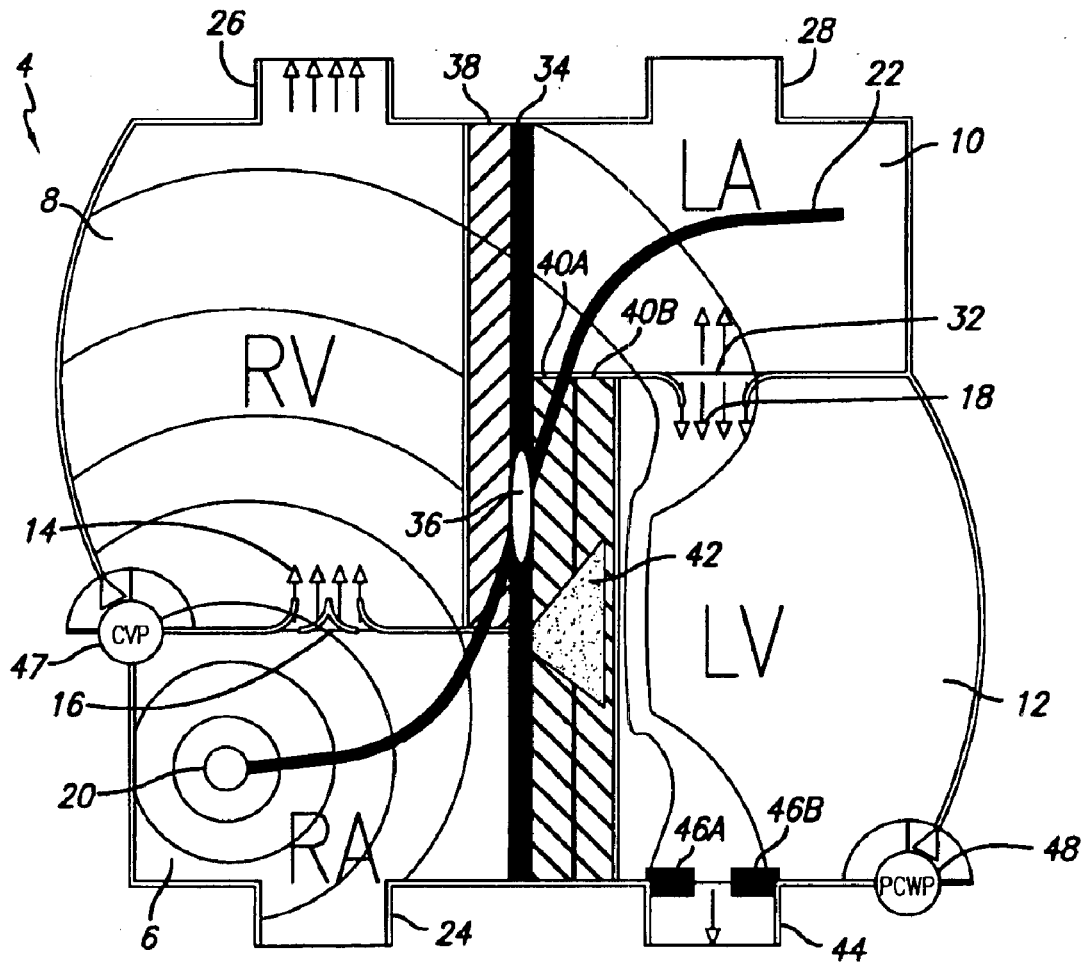
FIG. 2 shows one embodiment of the extended heart object.

FIG. 2 is an extended heart object display generally noted at 4. The extended heart object display 4, like the human heart, is divided into four chambers: a right atrium ("RA") metaphor 6; a right ventricle ("RV") metaphor 8; the left atrium ("LA") metaphor 10; and, the left ventricle ("LV") metaphor 12. As with all of the object displays, the extended heart object 4 and portions thereof may be displayed in black and white, in color or both and various meanings can be assigned to whether the object or portion are displayed in black and white or in color (when medical standards exist, they can be adhered to—e.g., normal zones in green, caution in yellow, violations of alarm conditions in red, etc.).

The data inputs for constructing the extended heart object are all available cardiac performance parameters including: filling pressures such as pulmonary capillary wedge pressure ("PCWP") 48 and central venous pressure ("CVP") 47; echo data dimensions of the of the RA, RV, LA and LV; valvular data, including aortic stenosis ("AS"), aortic insufficiency ("AI"), mitral stenosis ("MS"), mitral regurgitation ("MR"), tricuspid stenosis ("TS"), tricuspid regurgitation ("TR"), pulmonic regurgitation ("PR"), pulmonic stenosis ("PS"); septal holes, wall motion abnormalities, cardiac conduction data conveying heart rhythm information, electrocardiogram ("EKG") data related to ischemia and echocardiogram data showing decreased contractility of the RV and LV, hypertrophy, and/or diastolic dysfunction. Data can be obtained through an EKG that depicts conduction of electrical activity in the heart, and echocardiography to measure blood flow into and between the heart chambers, ventricle compliance and valve conditions, and a pulmonary artery catheter can be used for obtaining data relating to PCWP and CVP.

The four chamber shaped heart of the extended heart object 4, as shown in FIG. 2, is a reference frame for the "normal" relative proportion and anatomy of the human heart. In other embodiments, the heart could be represented as two, two chambered hearts for the pulmonary versus systemic regulations.

In the extended heart object, the RA, RV, LA and LV of the heart can expand or contract to show the filling state of the individual chambers. For example, in FIG. 2, the RV 8 and the LV 12 are in a filled state. This is demonstrated by the outward bulging of the individual chambers. If the filling pressures were low, the CVP and PCWP meters would point inwards and the display would show the RV and LV chambers to be scalloped inwards. The shape of the chambers conveys the status of FULL vs EMPTY. Located in-between the RA 6 and the RV 8 on the far left is a CVP meter 47 which moves in conjunction with the filling state of the RV 8. For example, if the RV is overfilled, the CVP meter 47 moves from the twelve o'clock position toward the eleven o'clock position or beyond. If the RV is under filled (not shown), the GyP meter moves from the twelve o'clock position to the one o'clock position or beyond. At the bottom of the LV chamber is the PCWP meter 48 which, like the CVP meter 47, moves according to the filling state of the LV 12.

Vertical lines (14 and 32), extending into and away from the heart chambers, illustrate the flow in and the flow out of blood from the various chambers. For example, global direction of flow is shown by the four arrows 14 from the RA 6 to the RV 8 through the tricuspid valve 16. The four arrows from the RA 6 to the RV 8 represents normal flow from the RA 6 to the RV 8. Mild regurgitation could be represented by three arrows in one direction and one arrow in the opposite direction. Arrows pointing in opposite direction as shown at 32 in FIG. 2, can have the following meanings: one arrow in the opposite direction to flow represents regurgitation (mild regurgitation); two arrows in the opposite direction represent (as shown at 32 in FIG. 2 at the mitral valve) represents two plus regurgitation (moderate regurgitation) and three arrows in the opposite direction represents three plus (severe regurgitation) [standard terms used in quantifying valve function from echocardiogram studies].

Also shown in FIG. 2 is sinus node 20 with conduction/rhythm information in the form of waves emanating outwardly in synchronization with an EKG trace. Extending from the sinus node 20 is the arterial bundle 22. Extending into the RA 6 is the venacava vein 24, extending from the RV 8 is the pulmonary artery 26, extending into the LA 10 is the pulmonary vein 28 and extending from the LV 12 is the aorta 44.

In the middle of the extended heart object 4 is a bold vertical line representing the septum 34. In the middle of the septum 34 is an oval shaped object 36 which represents the Atrio-ventricular node (AV-Node) and is intersected by the ventricular bundle (bundle of His 22). To the left of the septum 34 in the RV 8 is an elongated, rectangular shaded box 38 which represents the compliance state of the right ventricle. A reference box depicting the normal width is the same as the shaded box and therefore not visible. To the right of the septum 34 in the LV 12 are two vertically oriented rectangular, shaded boxes 40A and 40B, which illustrates non-compliant left ventricle because the shaded area extends beyond the reference box width that conveys the normal compliance state. Greater than normal compliance would be shown as a shaded area narrower than the reference box. Typically the reference box would be shown in a different color, such as purple, that would make it easy to see the patient state relative to the normal. As noted, to the left of the septum 34 is an another elongated, rectangular shaded box 38 and this represents a normal right ventricle. The RV and LV can be represented as being of normal, increased or decreased compliance.

Inside the two vertically oriented rectangular boxes 40A and 40B is a slightly offset triangle 42, shaded in color wherein the size of triangle 42 changes based on ischemic changes in the EKG in relation to ST-changes which show various conditions such as angina or ischemia.

Below LV 12 and extending from the extended heart object 4 is an example of stenosis of the aortic valve 44. The one arrow extending from the aortic valve 44 shows obstructed blood flow. Separating the aortic valve 44 and the LV 12 are two, side-by-side, bolded, horizontally oriented rectangles 46A and 46B which represent a thickened aortic valve. Thickening of any valve would be shown in the same manner. The extended heart object 4 of the present invention mimics the human heart and displays information in an intuitive manner to physicians or other medical personnel allowing for the display of a large quantity of information in a simplified manner.

Figures 1, 3:
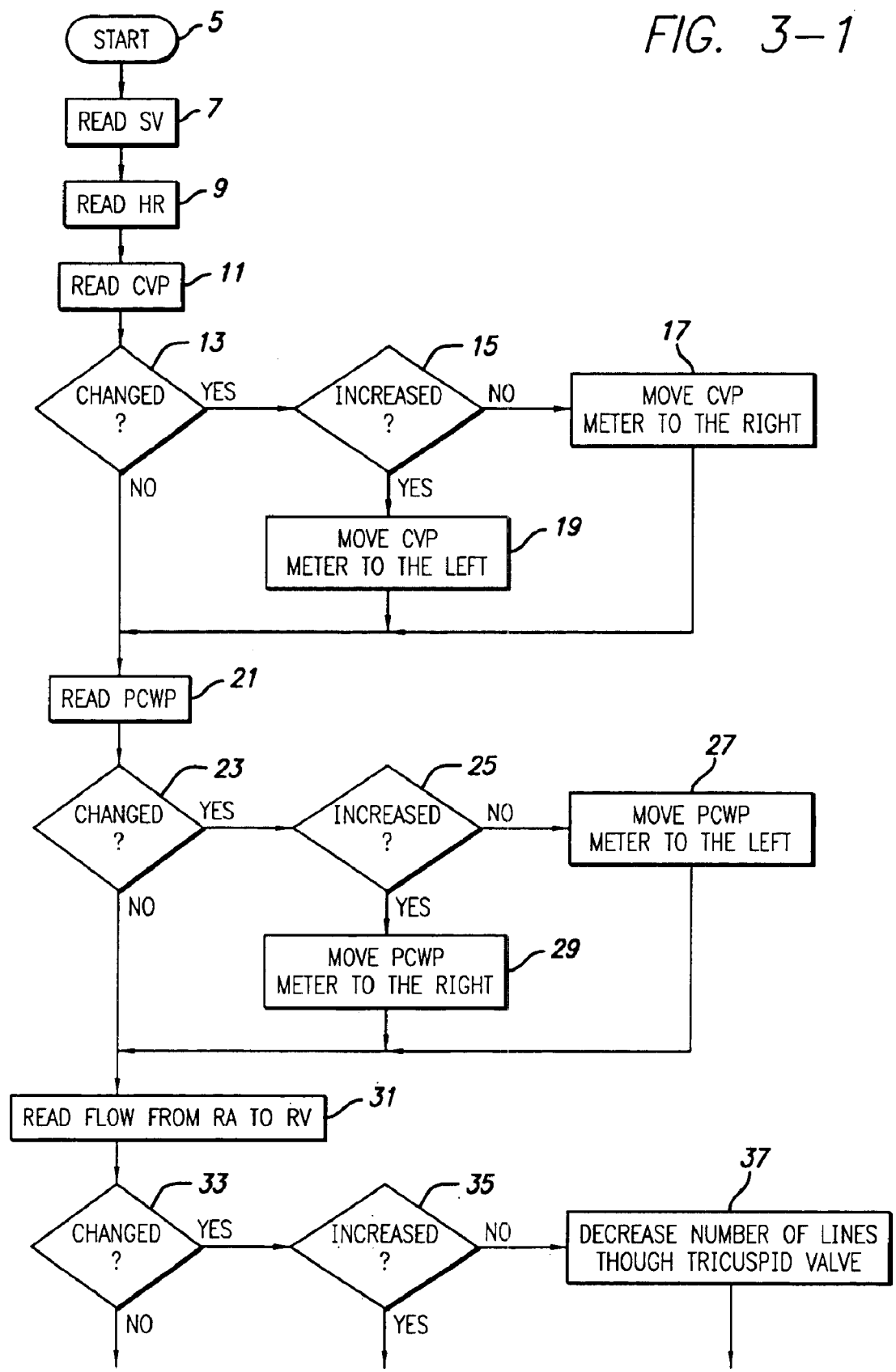
FIG. 3 is a flowchart illustrating one method that may be used to update the extended heart object.
Figures 2, 3:
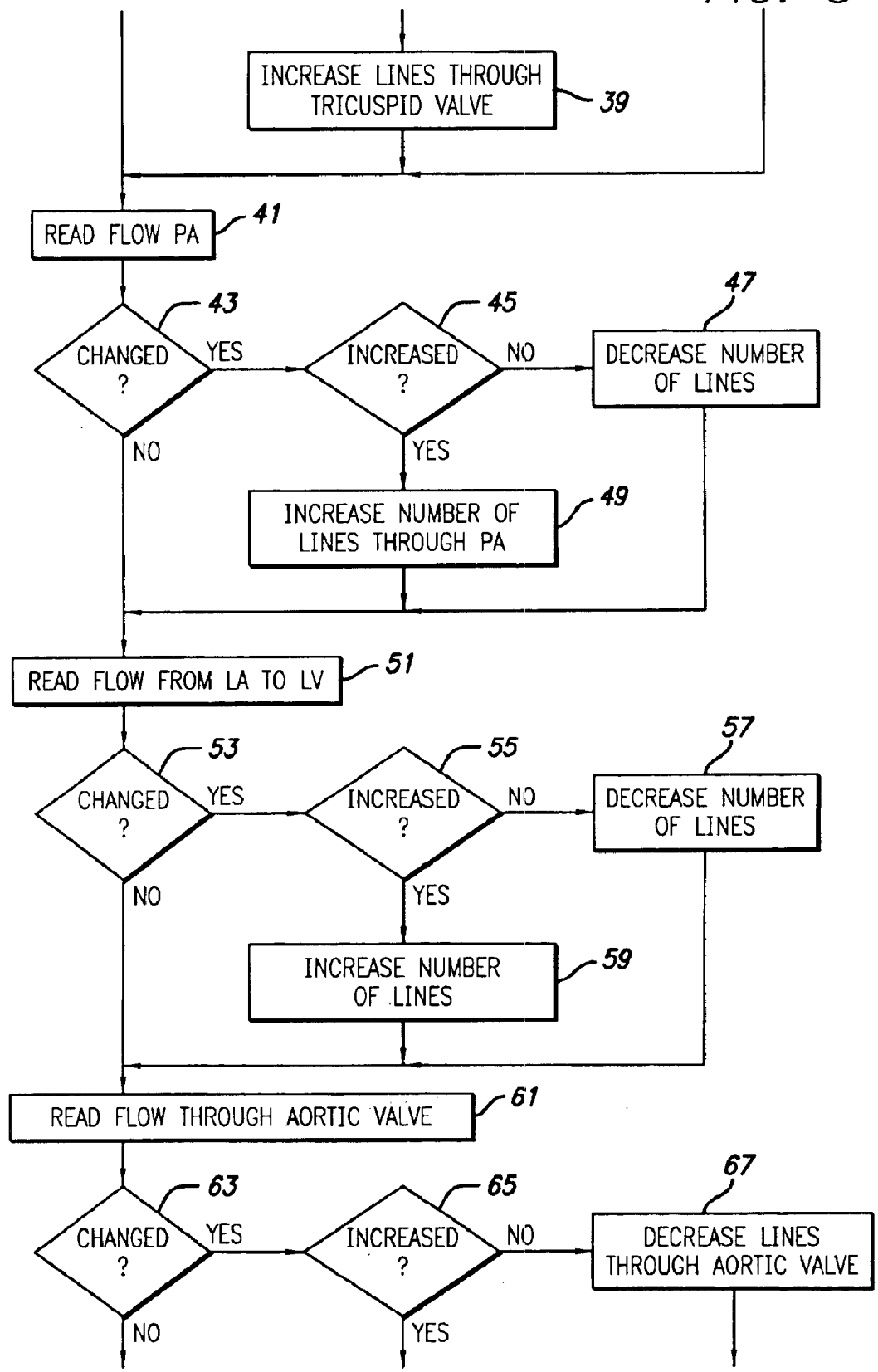
Figure 3:
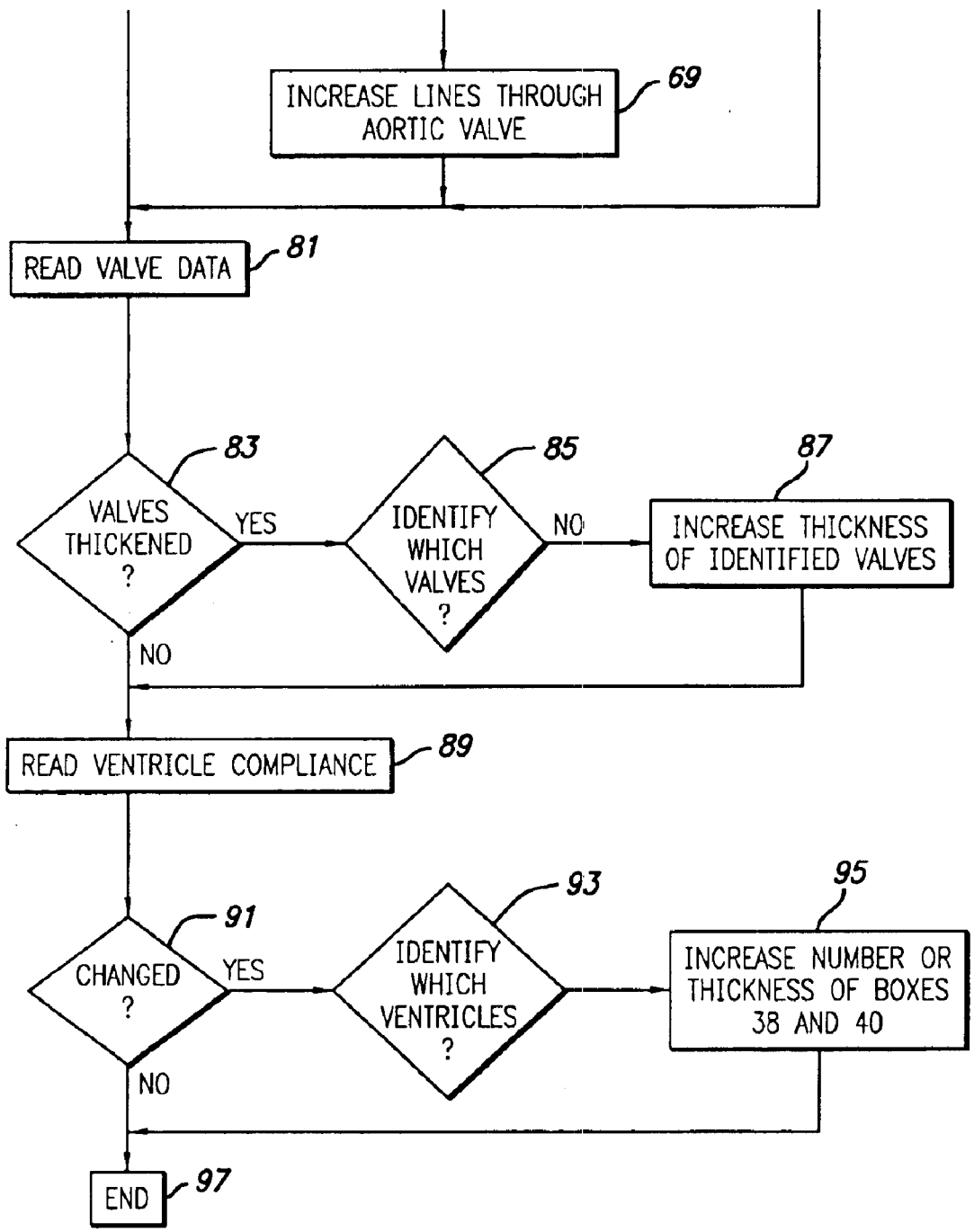

Referring now to FIG. 3, the process of updating the extended heart object begins when a start signal is transmitted by the user at start state 5. The start signal can be a keystroke or a mouse command that initiates the software to begin collecting data. After receiving the start command at state 5, the process moves to a state 7 where the stroke volume ("SV") is read. The stroke volume can be read from a table or a buffer in the computer system. After the SV is read, the process moves to a state 9 where the heart rate ("HR") is read.

Once data has been collected from a patient at any state, for example state 9, a "data in range" decision can be made. That is, the software compares the data collected at a given state. e.g., state 9, with known appropriate heart rates for a particular patient or previous heart rates read from previously collected data. If data at a given state, such as state 9, is not within preprogrammed ranges or are completely anomalous (i.e., out of range of any possible human heart rate), an error/exception handling routine can be initiated and the process begins again. The error/exception handling routine loops the software back to process step 9 and begins again. In this manner, false or erroneous information is not fed into the rest of the program. If data collected at a given state in appropriate ranges, the software pointer moves to the next process state.

After the HR is read, the process then moves to a state 11 where central venous pressure ("CVP") filling pressure is read. Like HR, CVP filling pressure may be collected from an EKG. A decision is then made at decision state 13 whether the CVP has changed since the last reading. If the CVP has changed, a determination is made at decision state 15 whether the CVP has increased or decreased. If the CVP has decreased, the process moves to a state 17 where the CVP meter is moved to the right and the outer boundary of the right ventricular metaphor moves inward to indicate a less filled right RV. In the alternative, if at decision state 15 the determination is made that the CVP has increased, the process moves to state 19 where the CVP meter is moved to the left and the outer boundary of the right ventricular metaphor moves outward to indicate a swollen or overfilled RV.

The process then moves to a state 21 where the pulmonary capillary wedge pressure ("PCWP") is read. The process then moves to a state 23 to determine whether the PCWP has changed since the last reading. If the PCWP has changed, a determination is made at state 25 as to whether the PCWP has increased or decreased. If the PCWP has decreased, the process moves to state 27 where the PCWP meter is moved to the left and the outer boundary of the LV heart chamber moves inward, or to the left, to indicate an under filled LV. If the value of the PCWP has increased, the process moves to state 29 where the PCWP meter is moved outward, or to the right, and the outer boundary of the LV metaphor moves outward to indicate an overfilled or swollen LV.

The process then moves to decision state 31 where the valve function from RA to RV is read. The process then moves to a state 33 where a determination is made whether the valve function from the RA to the RV has changed since the last reading. If the valve function has changed, the process moves to state 35 where if the valve flow has decreased, the process moves to state 37 where the number of lines extending from the RA to the RV through the tricuspid valve is decreased and bars showing stenosis are extended. If the valve flow from the RA to the RV has increased, the process moves to state 39 where if the valve function has increased, the number of lines extending from RA to RV through the tricuspid valve is increased and the bars of stenosis are shortened.

The process then moves to state 41 where the valve function from the RV through the pulmonary artery ("PA") is read. The process then moves to a state 43 where a determination is made whether the valve function from the RV through the pulmonary artery has changed since the last reading. If the valve function has changed, the process moves to state 45 to determine whether the valve flow has increased or decreased. If the valve flow has decreased, the process moves to state 47 where the number of lines extending from the RV through the pulmonary artery is decreased and bars showing stenosis are extended. If the valve flow has increased, the process moves to state 49 where the number of lines extending from the RV through the pulmonary artery is decreased and the bars of stenosis shortened.

The process then moves to state 51 where valve function from the LA to the LV through the mitral valve is read. The process then moves to a state 53 where a determination is made whether the blood flow from the LA to the LV has changed since the last reading. If the valve function has changed, the process moves to state 55 to determine whether the blood flow has increased or decreased. If the valve flow has decreased, the process moves to state 57 where the number of lines extending from the LA to the LV through the mitral valve is decreased and bars showing stenosis are extended. If the valve flow has increased, the process moves to state 59 where the number of lines extending from the LA to the LV through the mitral valve is decreased and the bars showing stenosis are shortened.

The process then moves to state 61 where valve function from the LV through the aortic valve 44 is read. The process then moves to a state 63 where a determination is made whether the valve function from the LV through the aortic valve has changed since the last reading. If the valve flow has changed, the process moves to state 65 to determine whether the valve flow has increased or decreased. If the valve flow has decreased, the process moves to state 67 where the number of lines extending from the LV through the aortic valve is decreased and the bars of stenosis are extended. If the valve flow has increased, the process moves to state 69 where the number of lines extending from the LV through the aortic valve is decreased and the bars of stenosis are shortened. If ST-changes are present on EKG, a triangle will be shown that represents a region of ischemia. The process then moves to state 89 where right and left ventricular compliance are read. The process then moves to state 91 where it is determined whether either the left ventricle or right ventricle has become less compliant (stiffened or thickened). If it is determined that either or both the RV or LV have become less compliant, the process then moves to state 93 to determine which or whether both ventricles have thickened. If either or both the RV or the LV have been identified as having thickened, rectangular boxes 38 and 40 are increased in width. This is shown in FIG. 2 where two rectangular boxes, 40A and 40B are shown to illustrate a mildly noncompliant RV and a moderately noncompliant LV. The process then ends at an end state 97.

B. Vascular Circuit Object

Figure 4:
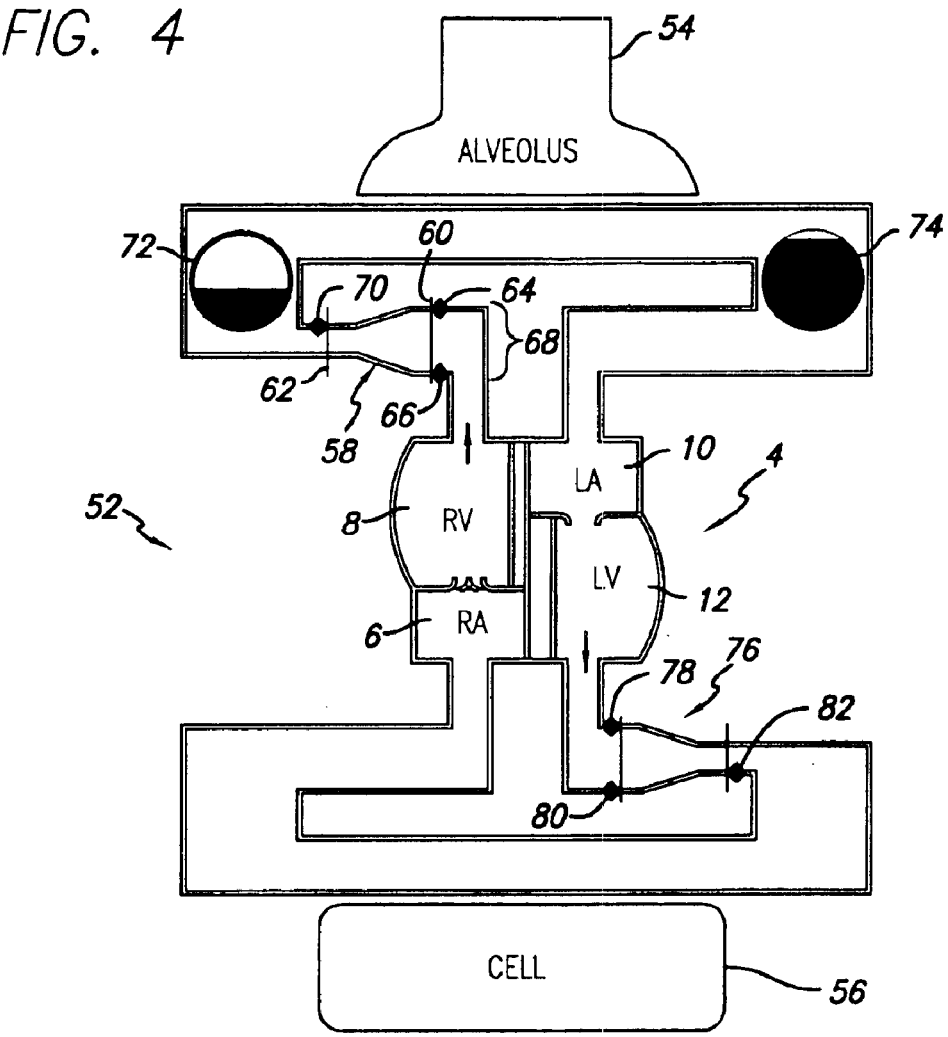
FIG. 4 shows one embodiment of the vascular circuit object.

FIG. 4 shows a vascular circuit object 52 which visually illustrates the oxygenation circuit of blood as it is pumped from the RA 6 and RV 8 of the heart 4 to the alveolus 54 back through the LA 10 and LV 12 of the heart 4 for oxygenation of the cell/tissues 56. Arrows depict the direction of the flow of blood from the RV 8 to the alveolus 54 and through the LV 12 to provide oxygen to the cell/tissues 56. The vascular resistor objects (58 and 76) are used by medical personnel to optimize the hemodynamic physiology of patients during surgery.

Located between the heart object 4 and the alveolus object 54 is a pulmonary vascular resistor object 58 which measures blood flow as it leaves the RV 8. Both vascular resistor objects 58 and 76 are used to display the blood flow equivalent of Ohm's law and represents the following equations:

(Mean Arterial Pressure)−(Central Venous Pressure)=(Cardiac Output)×(Systemic Vascular Resistance); and (Mean Pulmonary Arterial Pressure)−(Pulmonary Capillary Wedge Pressure)=(Cardiac Output)×(Pulmonary Vascular Resistance).

This data is displayed into linear scales relating to the pressure gradient for blood flow in the form of a "pipe" shaped object which is the pulmonary vascular resistor object 58 wherein blood flow is from right to left. A set of two Y axes, 60 and 62, produce the pipe shape of the vascular resistor object 58. Right Y axis 60 includes a mean arterial pressure (MAP) indicator 64 and a central venous pressure (CVP) indicator 66 which are in the form of diamond shaped objects. The distance between the MAP indicator 64 and the CVP indicator 66 indicates the blood input area 68 and represents the flow of blood into the pipe. A left Y axis 62 includes a cardiac output (CO) indicator 70 which reflects the calculated or measured cardiac output of the patient. As the cardiac output of the patient increases, the distance between the horizontal line intersecting the CO indicator and parallel X-axis beneath the CO increases as CO increases and the distance decreases as CO decreases.

Upstream of pulmonary vascular resistor object 58 is red blood cell object 72. Red blood cell object 72 reflects the level of oxygenation of the arterial blood prior to the blood reaching the alveolus 54. Arterial Oxygenation Content=(Arterial Oxygen Saturation)×(Hemoglobin)×(1.34). As displayed in FIG. 4, the amount of shading of the blood cell object 72 shows the percentage of oxygenation of the blood. As shown at 72 in FIG. 3, less than half of the blood is oxygenated (when less than half shaded, the cell is only half filled with oxygen).

As the blood passes through the lungs the blood becomes oxygenated. This is illustrated in FIG. 4 by the placement of the alveolus 54 between the left blood cell object 72 and the right blood cell object 74. Right blood cell object 74 illustrates the level of oxygenation of venous blood oxygenated by the lung 54. As with red blood cell object 72, the level of oxygenation of the blood leaving the alveolus is indicated by the percentage of shading of red blood cell 74. Both red blood cell objects mimic the in vivo state of oxygenation of the blood and are thus intuitive to physicians.

The blood then passes through the LA and the LV of the heart. As the blood leaves LV 12, it passes through systemic vascular resistor object 76 which operates in the same manner as described with pulmonary vascular resistor object 58. MAP indicator 78 and CVP indicator 80 represents the blood input area and represents the inflow of blood into the pipe. CO indicator 82 represents the calculated or measured cardiac output of the patient.

Figure 5:
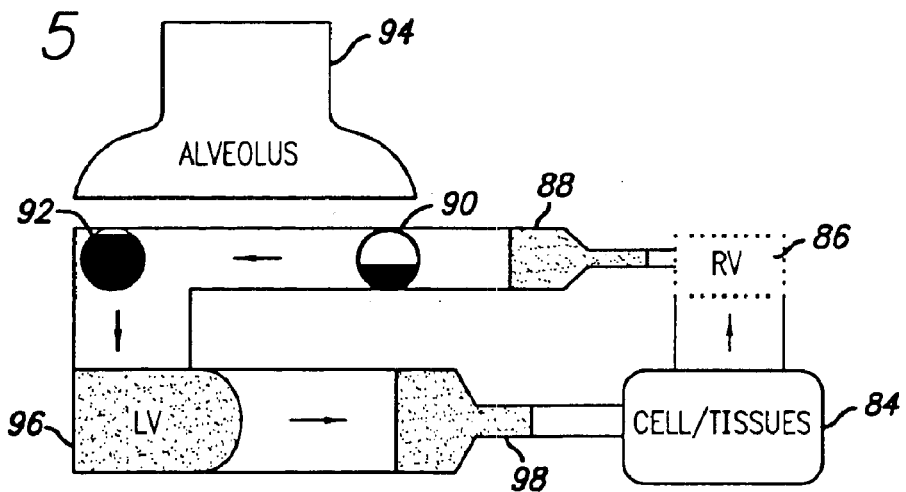
FIG. 5 shows another embodiment of the vascular circuit object, a split RV and LV version.

An alternative embodiment of the vascular circuit is shown in FIG. 5. In this embodiment, the extended heart object is omitted. In its place is an abbreviated heart object showing only the right ventricle ("RV") object 86. Blood flow is indicated by an arrow between the cell/tissue object 84 and RV object 86. In this embodiment, the chambers of the heart are split with the LV 96 downstream. Blood flow leaves RV 86 and enters into a pulmonary vascular resistor object 88 which functions in the same manner as vascular resistor object 58 of FIG. 4. Vascular resistor object 88 is used to display the blood flow equivalent to Ohm's law and the data is visually displayed in the form of object 58 as a pipe shaped object wherein blood flow is from right to left.

The area inside the pipe can be darkened to represent the represent the inflow of blood into the pipe and to aid visually. Both vascular resistance objects of FIG. 5 can have a MAP, CVP and CO indicators in the same manner as vascular resistor objects 58 and 76 of FIG. 4.

Downstream of the RV is a red blood cell object 90 which indicates the level of oxygenation of the blood leaving the RV which, as previously described, is visually indicated by the amount of shading of the red blood cell object 90. Further downstream from the red blood cell object 90, beyond alveolus 94, is a second red blood cell object 92. Red blood cell object 92 shows that the blood, at this point in the vascular circuit, is almost completely oxygenated. This is of course due to the fact that the blood is oxygenated by alveolus 94 located between the red blood cell objects 90 and 92.

Downstream from the red blood cell object 92 is LV 96 where blood passes through to the systemic vascular resistance object 98. Vascular resistance object 98 operates in a similar manner as the vascular resistance object 76 shown in FIG. 4. Blood flow is from the left to right and the widened area of the "pipe" illustrates a large inflow of blood to the and the narrowed darkened portion of the pipe represents the flow of blood from the to the cells/tissue 84. Blood then leaves the cell/tissue 84 area and enters the RV 86 and the cycle is repeated.

In an one embodiment, all of the information of extended heart object 2 is incorporated into the Vascular Circuit Object 52 in FIG. 4 and can be displayed. This information could be accessed or suppressed at the desire of the user.

Figures 1, 6:
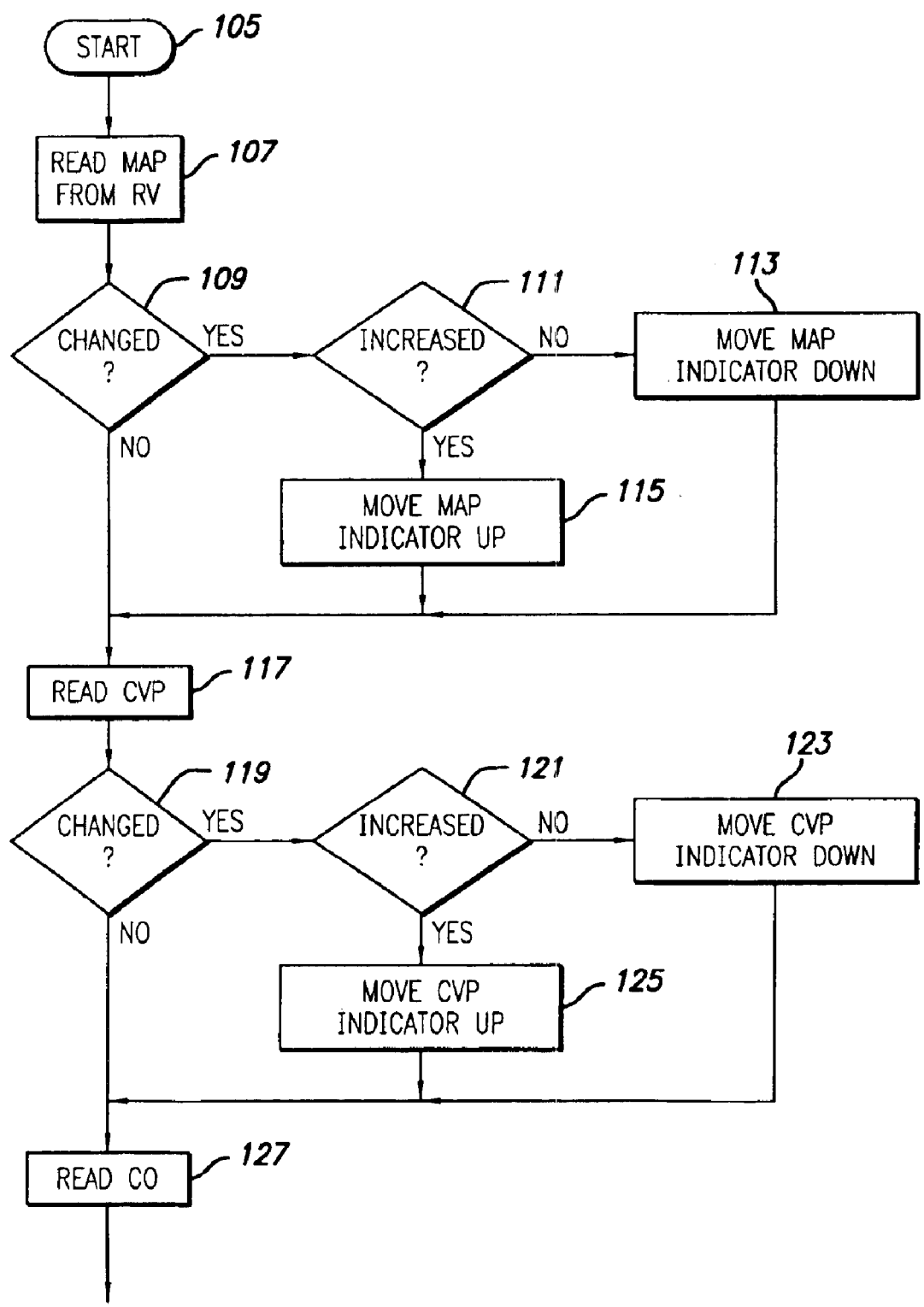
FIG. 6 is a flowchart illustrating one method that may be used to update the vascular circuit objects.
Figures 2, 6:
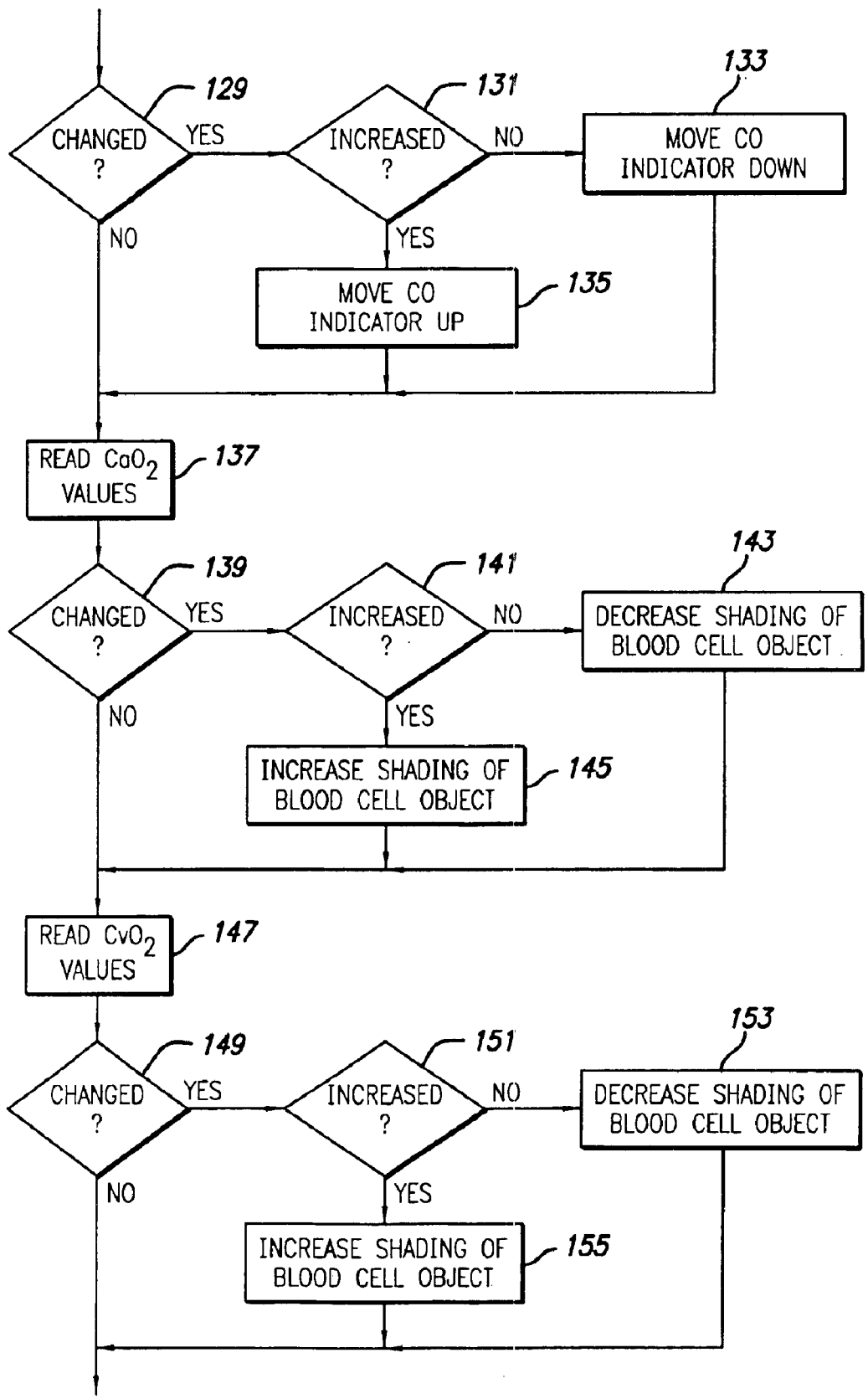

Referring to FIG. 6, a process of updating the Vascular Circuit Object is described. The process begins at start state 105 and then moves to a state 107 wherein the mean arterial pressure (MAP) is read. A determination is made at decision state 109 whether the MAP has changed since the last reading. If the MAP has changed, the process moves to state 111 to determine whether the MAP has increased or decreased. If MAP has decreased, the process moves to state 113 where MAP indicator 64 is moved downward along Y-axis 60. If a determination was made at state 111 that MAP has increased, the process moves to state 115 where the MAP indicator moves upward along Y-axis 60.

The process then moves to state 117 wherein the central venous pressure ("CVP") of the patient is read. A determination is made at decision state 119 whether the CVP has changed since the last reading. If the CVP has changed, the process moves to state 121 to determine whether the CVP has increased or decreased. If the CVP has decreased, the process moves to state 123 wherein the CVP indicator 66 moves down Y-axis 60. If the CVP has increased, the process moves to state 125 where the CVP indicator 66 moves up Y-axis 60.

The process then moves to state 127 where the cardiac output (CO) is read. A determination is made at state 129 whether or not the CO has changed since the last reading. If the CO has changed, the process moves to state 131 to determine whether the CO has increased or decreased. If the CO has decreased, the process moves to state 133 wherein the cardiac output indicator 70 is moved downward along Y-axis 62. If a determination is made at state 131 that the CO has increased, the process moves to state 135 wherein the cardiac output indicator 70 moves up Y-axis 62.

The process then moves to a state 137 where it reads the $CaO_2$ value of the blood prior to the blood being oxygenated by the lungs. This value could be read from a data table or from any type of memory storage in the computer system.

Once the $CaO_2$ values are read, the process moves to state 139 to determine whether the $CaO_2$ value has changed from the last reading. If the $CaO_2$ value has changed, the process moves to state 141 to determine whether the $CaO_2$ value has increased or decreased since the last reading. If the $CaO_2$ value has decreased, the process moves to state 143 and the level of shading of red blood cell object 72 is decreased. However, if the process determined that the $CaO_2$ value has increased, the process moves to state 145 where the level of shading of red blood cell object 72 is increased.

The process then moves to state 147 where the $CvO_2$ value of the blood is read after the blood is oxygenated by the lungs. This value could be read from a data table or from any type of memory storage in the computer system. Once the $CvO_2$ value is read, the process moves to state 149 to determine whether the $CvO_2$ value has changed since the last sampling. If the $CvO_2$ value has changed, the process moves to state 151 to determine whether the $CvO_2$ has increased or decreased since the last reading. If the $CvO_2$ value has decreased, the process moves to state 153 and the level of shading of red blood cell object 74 is decreased. However, if the process determines that the $CvO_2$ value has increased, the process moves to state 155 where the level of shading of the red blood cell object 74 is increased.

Returning to FIG. 4, the blood then passes through LA 10 and LV 12 of Vascular Circuit 52 and then the process moves to systemic vascular resistor object 76. Systemic vascular resistor object 76 works in the same manner as pulmonary vascular resistor object 58 and the process steps will not be repeated again.

C. Cardiopulmonary Bypass Object

Figure 7:
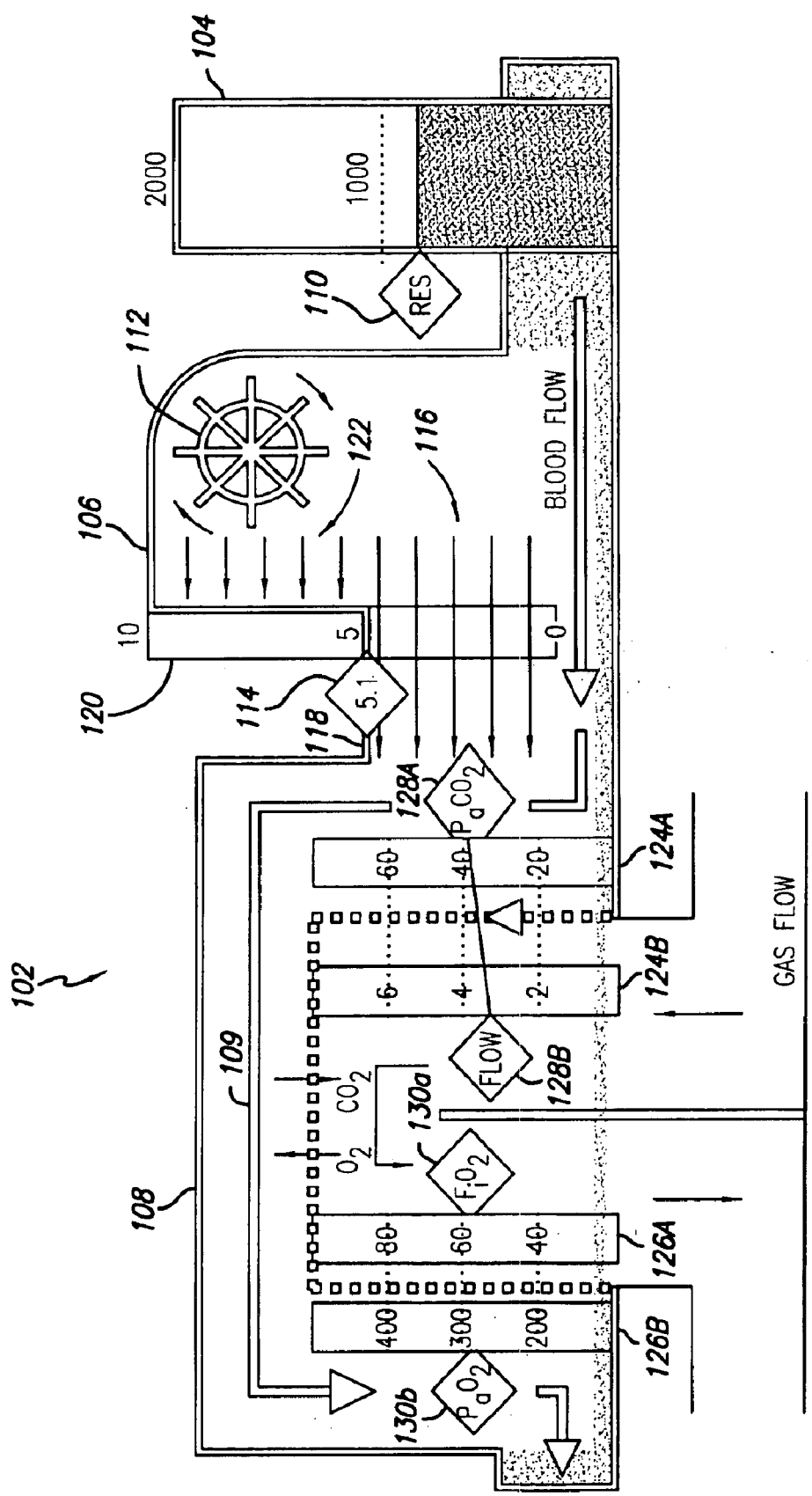
FIG. 7 shows one embodiment of the cardiopulmonary bypass object.

As shown in FIG. 7 is a cardiopulmonary bypass object 102. The cardiopulmonary bypass object 102 illustrates information on the oxygenation of blood diverted from the heart during a cardiopulmonary bypass procedure. The cardiopulmonary bypass object 102 is comprised generally of three components (reading right to left in FIG. 7): 1) a venous reservoir object 104; 2) a roller pump object 106; and, 3) an oxygenator object 108.

The venous reservoir object 104 graphically illustrates the quantity of blood in the venous reservoir. In the illustration of FIG. 7, a diamond shaped marker 110 shows the level of stored venous blood and moves up and down metered scale 104 as the volume of blood fluctuates. Blood flow moves from the venous reservoir 104 to the roller pump object 106. Roller pump object 106 depicts the state of the pump as either being "off" or "on" by showing the roller 112 rotating clockwise or counter clockwise when "on" or static or unmoving when the pump is "off". The roller 112 rotates clockwise or counter-clockwise depending on where the pump is located and the underlying global direction of blood flow. Total blood flow from the roller pump object is depicted by a diamond shaped marker 114 which, in the example of FIG. 7, has the number 5.1 located therein which depicts 5.1 L/min blood flow into the oxygenator object 108. Horizontally extended lines 116 extending from roller pump to the oxygenation object 108 also depict blood flow. Five (5) arrows are shown which roughly corresponds to the 5.1 number in diamond shaped marker 114 representing 5.1 liters per minute of blood flow to oxygenator object 108.

Intersecting diamond shaped marker 114 is a bold line 118 oriented above and parallel to the five (5) arrows 116. Line 118 connects the roller pump object 106 to the blood oxygenator object 108 and also intersects and moves up and down a vertically oriented scale 120. Scale 120 is metered (L/min) to show blood flow from the roller pump object 106 to the blood oxygenator object 108. The shorter dashed lines 122 pointing to scale 120 show potential unused blood flow. As blood flow increases, horizontal bold line 118 moves vertically upward in a Y-axis direction (but remains horizontally oriented) and shorter dashed lines 122 lengthen and become solid lines and pass through under bold line 118 illustrating actual blood flow. As blood flow decreases, horizontal bold line 118 moves vertically downward and lines 116 shorten into shorter dashed lines 122.

Blood flow is then shown moving from the roller pump object 106 to oxygenator object 108 as shown by the bold arrow 109 (which is a static line) moving through the top of oxygenator object 108. Oxygenator object 108 graphically illustrates the relationship of blood flow and gas flow and concentration across a diffusion surface represented by the dashed line. Two sets of vertically oriented rectangles 124A, 124B and 126A, 126B, side-by-side, measure blood flow, gas flow and gas concentration. For example, 124A is metered to measure arterial carbon dioxide concentration ($PaCO_2$) in the bloodstream while 124B is metered to measure gas flow (oxygen) into the bloodstream. 126A measures fraction of inspired oxygen in the blood stream ($FiO_2$) and 126B measures mixed arterial oxygen tension ($PaO_2$). Two diamond shaped markers, one (128A) measuring mixed arterial carbon dioxide tension $PaCO_2$ and the other gas flow (128B) are shown and can be connected by a horizontal line which helps the user visualize the interrelationship of the $PaCO_2$ parameter of the blood and gas flow. Two other markers visually displaying $FiO_2$ 130A and the other marking displaying $PaO_2$ (130B) are also displayed.

In an alternate embodiment, a meter could be displayed, adjacent or near the $PaCO_2$ meter, for measuring in real time the amounts of the anesthetic isoflourine both administered and respired. In the same manner as with the other meters for measuring various values, a marker could be used for measuring the amounts of administered isofluorine and another marker for measuring amounts of expired isoflourine. Both markers would move vertically up and down the meter (which would measure isolfluorine in ml/L). When the meters indicate two different values, this would indicate to the physician that the administered and measured isofluorine amounts are different telling the physician the amount of anesthetic in the patient.

Figures 1, 8:
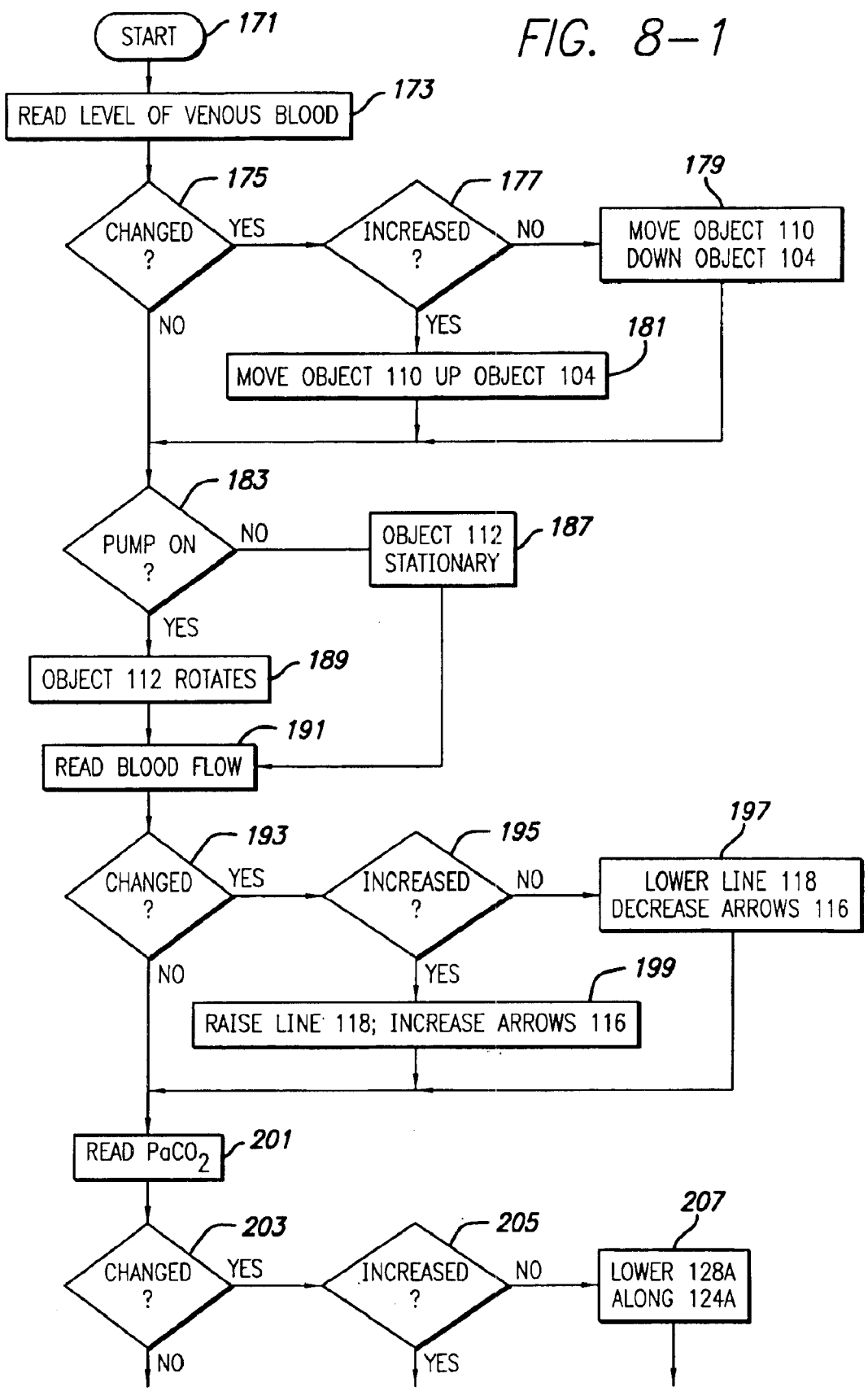
FIG. 8 is a flowchart of one method that may be used to update the cardiopulmonary bypass object.
Figures 2, 8:
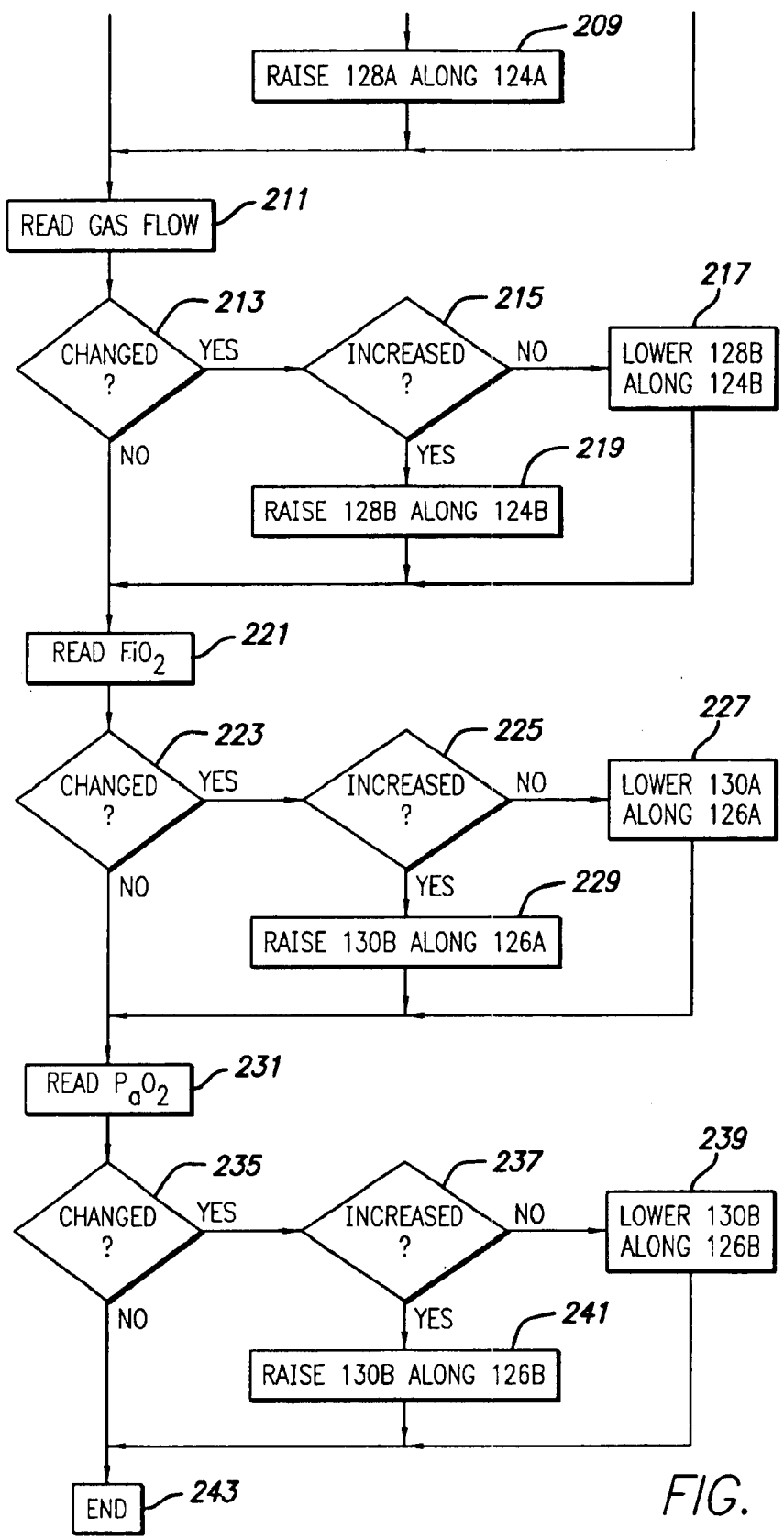

Referring to FIG. 8, a process for updating Cardiopulmonary Bypass Object 102 is described. The process begins at start state 171 and then moves to state 173 wherein the level of stored venous blood in venous reservoir 104 is read. The process then moves to state 175 wherein the process determines whether the level of stored venous blood has changed since the last reading. If the level of stored venous blood has changed, the process moves to state 177 to determine whether the level of stored venous blood has increased or decreased. If the level has decreased, the process moves to state 179 where if the level of stored venous blood has decreased, diamond 110, which acts as a marker along the venous reservoir object 104, moves downward along venous reservoir object 104. If it is determined that the level of stored venous blood has increased, the process moves to state 181 where the diamond 110 moves upward along object 104.

The process then moves to state 183 where a determination is made whether the pump is activated. If the pump is not activated, the process moves to state 187 where object 112 is made stationary. However, if the pump is activated, that is "turned on", the process moves to state 189 where the pump object rotates in the clockwise direction.

The process then moves to state 191 where the quantity of blood flow from roller pump object 106 to oxygenator object 108 is read. The process then moves to state 193 where it is determined whether the amount of blood flow from roller pump object 106 to oxygenator object 108 has changed. If it is determined that there has been a change, the process moves to state 195 where a determination is made whether the amount of blood flow from roller pump object 106 to oxygenator object 108 has increased or decreased. If it has decreased, the process moves to state 197 and line 118, along with marker 114, move down scale 120 in the Y direction and the number of horizontally extended arrows 116, which correspond to the liters of blood flow from the roller pump object 106 to the blood oxygenator object 108, are decreased accordingly. If the blood flow from roller pump object 106 to the blood pump object 108 has been determined to have increased at state 195, the process moves to state 199 and the line 118, along with marker 114, are moved upward along meter 120 in the Y direction and the number of horizontally extended arrows 116 are increased accordingly.

The process then moves to state 201 where the $PaCO_2$ value of the blood is read. The process moves to state 203 where it is determined if the $PaCO_2$ value has changed. If the value has changed, the process moves to state 205 where it is determined whether the $PaCO_2$ value has increased or decreased. If the $PaCO_2$ value has decreased, the process moves to state 207 where diamond marker 128A lowers along meter 124A and reflects the appropriate $PaCO_2$ value. If it is determined that the $PaCO_2$ value has increased, the process moves to state 209 where diamond shaped marker 128A raises along meter 124A to reflect the updated $PaCO_2$ value.

The process then moves to state 211 where the gas flow, as shown in FIG. 7, is read. The process then moves to state 213 where it is determined whether the gas flow has changed since the last reading. If the gas flow has changed, the process moves to state 215 where it is determined whether the gas flow has increased or decreased. If the gas flow has decreased, the process moves to state 217 where marker 128B, which marks the flow of gas as shown by meter 124B, is lowered along meter 124B to the sampled gas flow measurement. However, if it is determined that the gas flow has increased, the process moves to state 219 where marker 128B is raised along meter 124B to the corresponding value.

The process then moves to state 221 where the $FiO_2$ value of blood is read. The process then moves to state 223 where it is determined whether the $FiO_2$ value of the blood has changed since its last reading. If it has changed, the process moves to step 225 where it is determined whether the $FiO_2$ value has increased or decreased since the last sampling. If it has decreased, the process moves to state 227 where marker 130a is lowered along meter 126A in the Y direction to the appropriate reading. If it is determined at state 225 that the $FiO_2$ value has increased, the process moves to state 229 and marker 130A moves upward along meter 126A to the corresponding $FiO_2$ value reading.

The process then moves to state 231 where the $PaO_2$ value is read. A determination is then made at decision state 235 whether the $PaO_2$ value of the blood has increased or decreased since the last sampling. If it is determined that the $PaO_2$ value has changed, the process moves to state 237 where it is determined whether the $PaO_2$ value has increased or decreased. If it is determined that the $PaO_2$ value has decreased, the process moves to state 239 where marker 130B, which marks the $PaO_2$ value along meter 126B, is lowered along meter 126B to mark the last measured $PaO_2$ value. If it determined at state 237 that the $PaO_2$ value has increased, the process moves to state 241 and marker 130B is raised to the appropriate $PaO_2$ value along meter 126B.

D. Ventilator State Object

Figure 9:
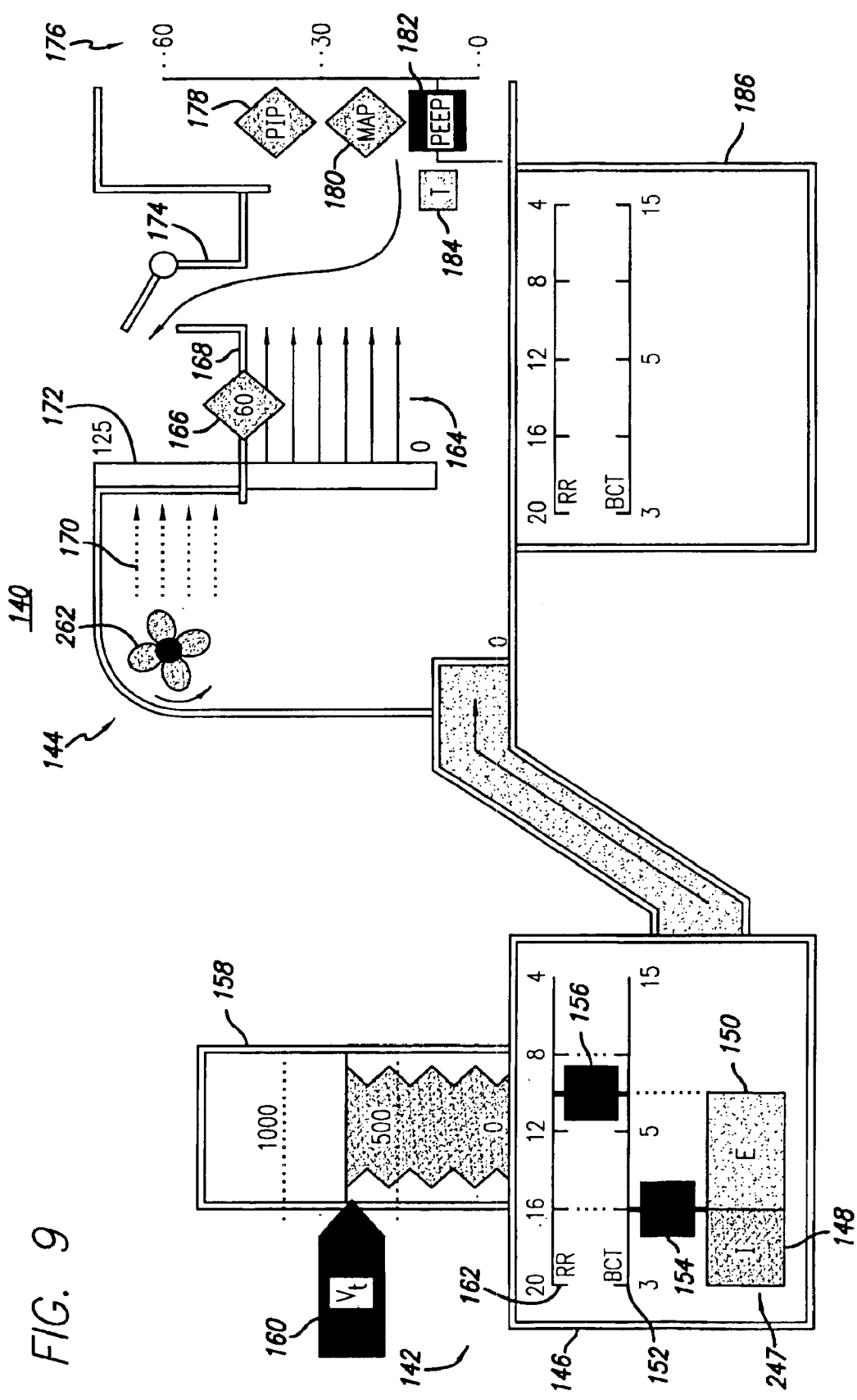
FIG. 9 shows one embodiment of the ventilator state object.

As shown in FIG. 9 is Ventilator State Object 140. Ventilator State Object 140 has two major components: a volume ventilator object 142 and a pressure ventilator object 144. Many ventilators are either volume or pressure ventilators and some ventilators are mixed volume/pressure. The object display of FIG. 9 allows physiological display information as to both types of ventilators or a mixed volume-pressure ventilator. However, when in a volume mode, the pressure ventilator settings are shaded gray or shaded in another color. Likewise, when in a pressure mode, the volume ventilator settings are shaded gray or shaded in another color.

The volume ventilator object 142, which may be used in conjunction with a standard volume ventilator, is comprised of a rectangular box 146 which displays information related to respiratory rate ("RR"), breath cycle time ("BCT"), inspiration time ("I"), expiration time ("E"), I:E ratio and volume setting of the ventilator. Much of this data can be obtained from the RS232 serial ports on most ventilators.

A shaded rectangle 247 is divided between a darker shaded portion 148 which represents inspiratory time and another more lightly shaded portion of the rectangle 150 which represents expiratory time 150. Both inspiratory and expiratory time added together equal breath cycle time "BCT" which is shown in lower BCT meter 152.

As shown in FIG. 9, the I portion of the BCT is 1 second with the shading between the three and four second mark. The expiratory time portion ("E" portion) is 1.5 seconds (1:1.5 I:E ratio) which is the difference between 4 and 5.5 seconds of the BCT meter. Marker 154 shows the division between inspiratory time and expiratory time of the breath cycle. As the breath cycle shortens or lengthens based upon volume settings, rectangle 247 will also shorten or lengthen.

Above BCT meter 152 is respiratory rate ("RR") meter 162. Respiratory rate is defined as the number of breaths per minute and is set by the physician on the ventilator. In FIG. 9, the RR is set at 10 breaths/minute as is seen on the RR meter 162. The lower the respiratory rate, the longer the BCT. Square marker 156 gives the user a clear indication between BCT and RR.

Above rectangular box 146 is a bellows object 158 which visually displays the volume of air being pushed into the lungs. In the case of FIG. 9, 700 cubic centimeters of air are shown as being pushed into the lungs by the ventilator. Marker 160 gives a clear indication of the setting of the ventilator.

Pressure ventilator object 144 is an alternate ventilator object useful with pressure ventilators. Located within the pressure ventilator object 144 is a propeller object 262 which rotates in the counter-clockwise direction to illustrate flow of air from the pressure ventilator to the patient. When the pressure ventilator is off or not functioning, the propeller object 262 is static and does not rotate. In an alternative embodiment, the rotational velocity of the propeller object 262 can indicate the level of air flow from the pressure ventilator to the patient.

Flow from the pressure ventilator to the patient is illustrated in the series of horizontal lines 164 extending from the pressure ventilator object 144 to the patient. The six horizontal lines indicate that 60 liters/min of air is flowing from the pressure ventilator to the patient. This is also illustrated by the diamond shaped object 166 which displays the number of liters of air per minute which is flowing to the patient. Horizontal bold line 168 intersects object 166 and the line 168 moves up and down depending on air flow to the patient.

The series of four horizontal lines 170 adjacent to propeller object 262 and above horizontal lines 164 illustrate potential unused air flow. Meter 172 also illustrates the quantity of liters of air per minute to the patient. The series of horizontal lines 164 are only displayed during inspiration of the patient's breath. During inspiration, the horizontal lines are turned off and are not shown.

To the right of object 166 is valve 174 which is closed while the patient is inspiring and open when the patient is expiring (when the pressure ventilator is activated). At the right hand side of the pressure ventilator object 144 is a meter 176 for displaying peak inspiratory pressure ("PIP") and mean airway pressure ("MAP"). Meter 176 has a diamond shaped object 178 for displaying PIP levels and a diamond shaped object 180 for displaying MAP levels. Both objects move up and down meter 176 depending on the PIP and MAP levels. PIP and MAP levels are sometimes set by the physician depending on the ventilation mode.

Beneath the PIP and MAP indicators is positive end expiratory pressure ("PEEP") indicator 182. PEEP may be a triggered setting (patient initiated setting) which is indicated by the presence of box 184 which has a "T" inside of the box. PEEP can also be measured wherein the PEEP indicator 182 would be diamond shaped and box 184 would not be shown. When measured, PEEP indicator 182 moves vertically up and down meter 176.

Beneath pressure ventilator object 144 is meter 186 which provides information on respiratory rate ("RR") and breath cycle time ("BCT") of the pressure ventilator in the same manner as with the volume ventilator. In an alternative embodiment, a similar configuration of the volume ventilator or pressure ventilator object can be positioned over the volume ventilator 142.

Figures 1, 10:
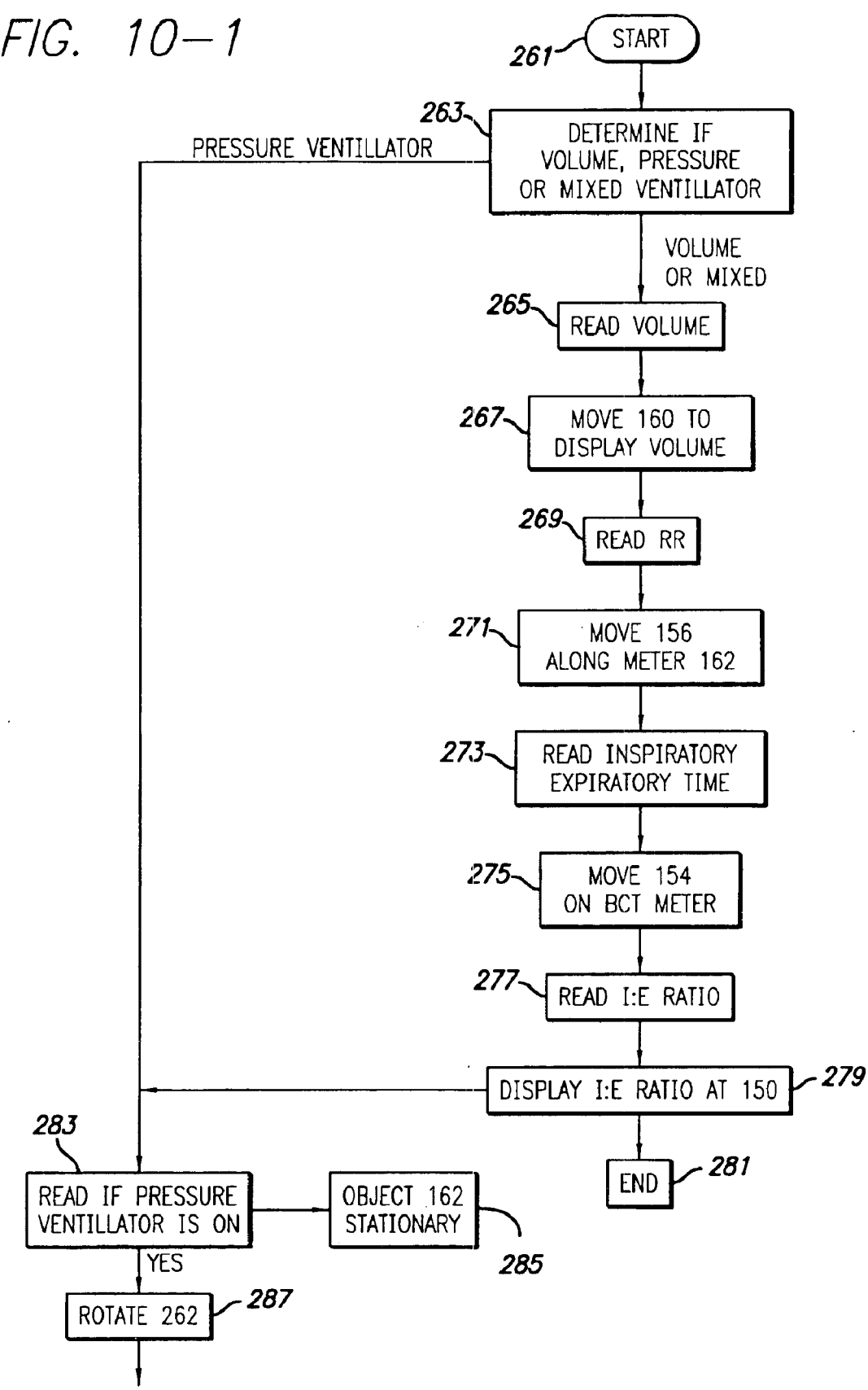
FIG. 10 is a flowchart of one method that may be used to update the ventilator state object.
Figures 2, 10:
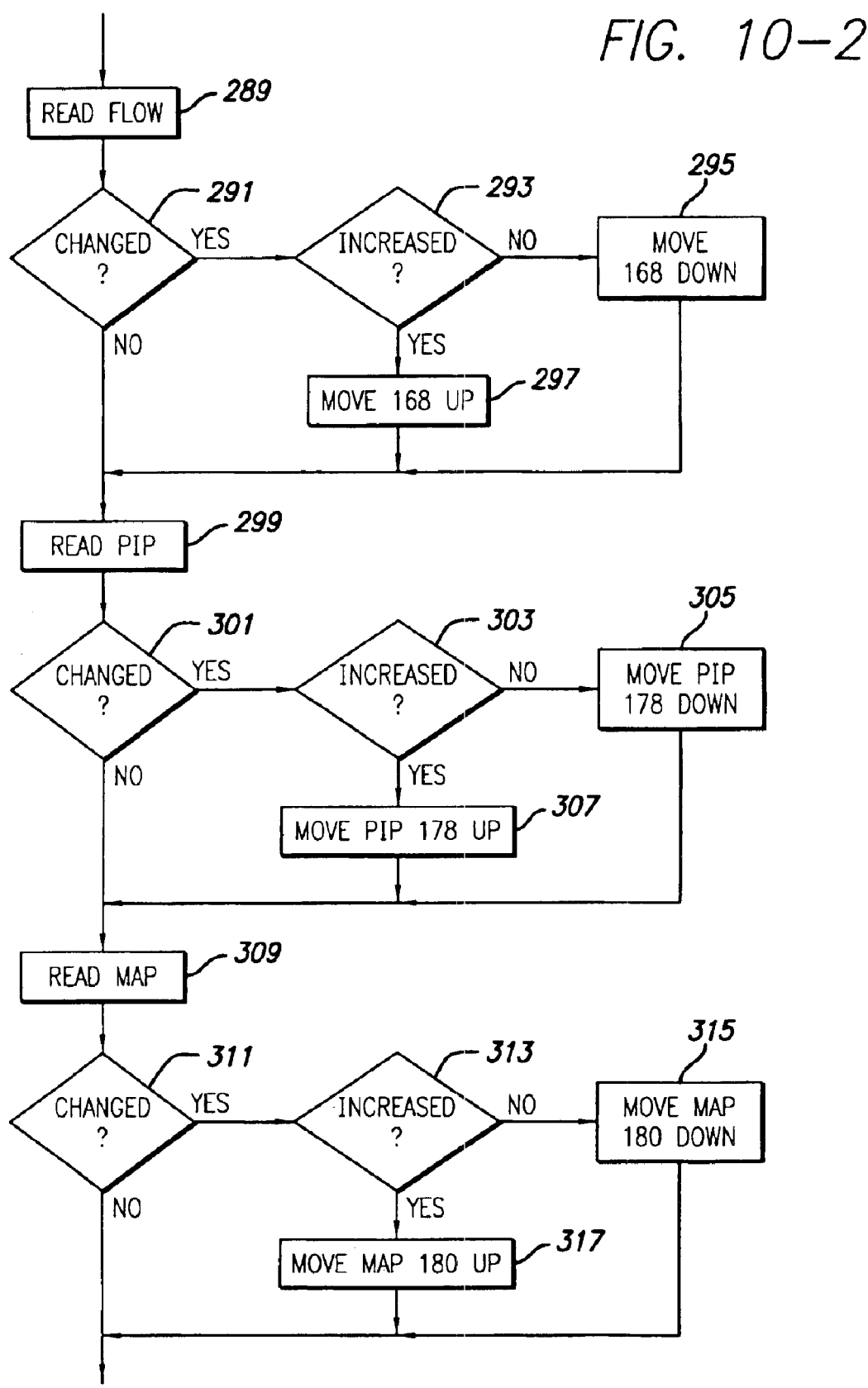
Figures 3, 10:
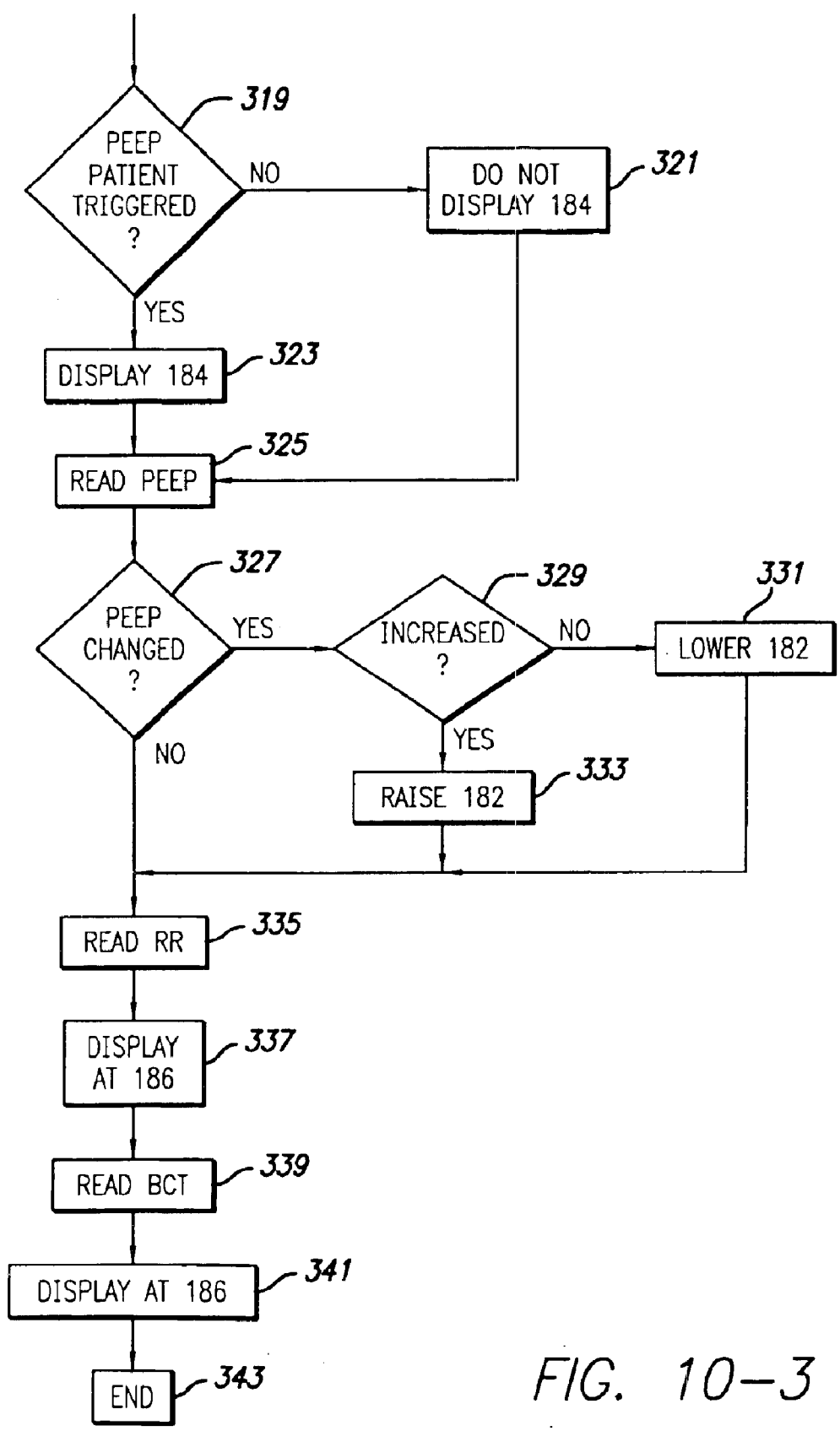

Referring to FIG. 10, the process starts of modulating the ventilator state object starts at 261. The process moves to state 263 where it is determined whether the ventilator is a volume ventilator, pressure ventilator or a mixed volume/pressure ventilator. If the process determines that it is a pressure ventilator, the process moves to state 283. If the process determines that it is a volume ventilator, the process moves to state 265 where the process reads the volume of air being delivered to the patient's lungs. As stated previously, the volume of air pushed into the patient's lungs is a set parameter. After reading the volume, the process moves marker 160 to the corresponding reading on bellows object 158. The process then moves to state 269 and reads the respiratory rate ("RR") set by the physician. The process then moves to state 271 where marker 156 is moved to correspond to the RR along meter 162. The process then moves to state 273 where inspiratory and expiratory times are read. The process then moves to state 275 where breath cycle time (the sum of inspiratory and expiratory time) is displayed on meter 152. The process then moves to state 277 where the inspiratory/expiratory ("I:E") time ratio is read. The process then moves to state 279 where the I:E ratio is displayed.

If the ventilator is only a volume ventilator, the process moves to end state 281. If the ventilator is a pressure ventilator the process moves from state 263 to state 283. Or, if the ventilator is a mixed pressure/volume ventilator, the process moves from state 279 to state 283. At state 283, the process determines if the pressure ventilator is on. If the pressure ventilator is off, the process moves to state 285 where propeller object 262 is made stationary. If the pressure ventilator is on, the process moves to state 287 where the propeller object 262 is rotated in the counter-clockwise direction. The process then moves to state 289 where air flow to the patient is read. The process then moves to state 291 where it is determined if the air flow has changed. If the air flow has changed, the process then moves to state 293 where it is determined whether the airflow has increased or decreased. If the airflow has decreased, horizontal line 168 along with air flow marker 166 is moved downward along meter 172. If it is determined at state 293 that the air flow has increased, the process moves to state 297 and horizontal line 168 and marker 166 are moved up meter 172 to reflect the sampled air flow.

The process then moves to state 299 where the peak inspiratory pressure ("PIP") is read. The process then moves to state 301 where it is determined whether the PIP has changed. If the PIP has changed, the process moves to state 303 where it is determined whether PIP has increased or decreased. If PIP has decreased, the process moves to state 305 where the PIP indicator 178, moves downward along meter 176. If it is determined at state 303 that PIP has increased, the process moves to state 307 where PIP indicator 178 moves up meter 176 to reflect the PIP reading.

The process then moves to state 309 where the mean airway pressure ("MAP") is read. The process then moves to state 311 where it is determined whether the MAP has changed. If the MAP has changed, the process moves to state 313 where it is determined whether the MAP has increased or decreased. If the MAP has decreased, the process moves to state 315 where MAP indicator 180 is moved down meter 176. If it is determined at state 313 that the MAP has increased, the process moves to state 317 and MAP indicator 180 is moved up meter 176 to reflect the higher MAP value.

The process then moves to state 319 where the system determines if the PEEP is patient triggered. If the PEEP is not patient triggered, the process moves to state 321 where box 184 is not displayed. If it is determined that PEEP is patient triggered, the process moves to state 323 where box 184, with the letter "T" located therein indicating that PEEP is patient triggered, is displayed.

The process then moves to state 325 where PEEP is read. The process then moves to state 327 where it is determined whether PEEP has changed. If PEEP has changed, the process moves to state 329 where it is determined whether PEEP has increased or decreased. If PEEP has decreased, the process moves to state 331 and PEEP indicator 182 is lowered along meter 176. If it is determined that PEEP has increased, the process moves to state 333 where PEEP indicator 182 moves upward along meter 176 to reflect the PEEP reading.

The process then moves to state 335 where respiratory rate ("RR"), which is set by the physician, is read. The process then moves to state 337 where RR is displayed at 186. The process then moves to state 339 where breath cycle time ("BCT") is read. The process then moves to state 341 where BCT is displayed at 186. The process then moves to end state 343.

E. Combined Lung and Ventilator Object

Figure 11:
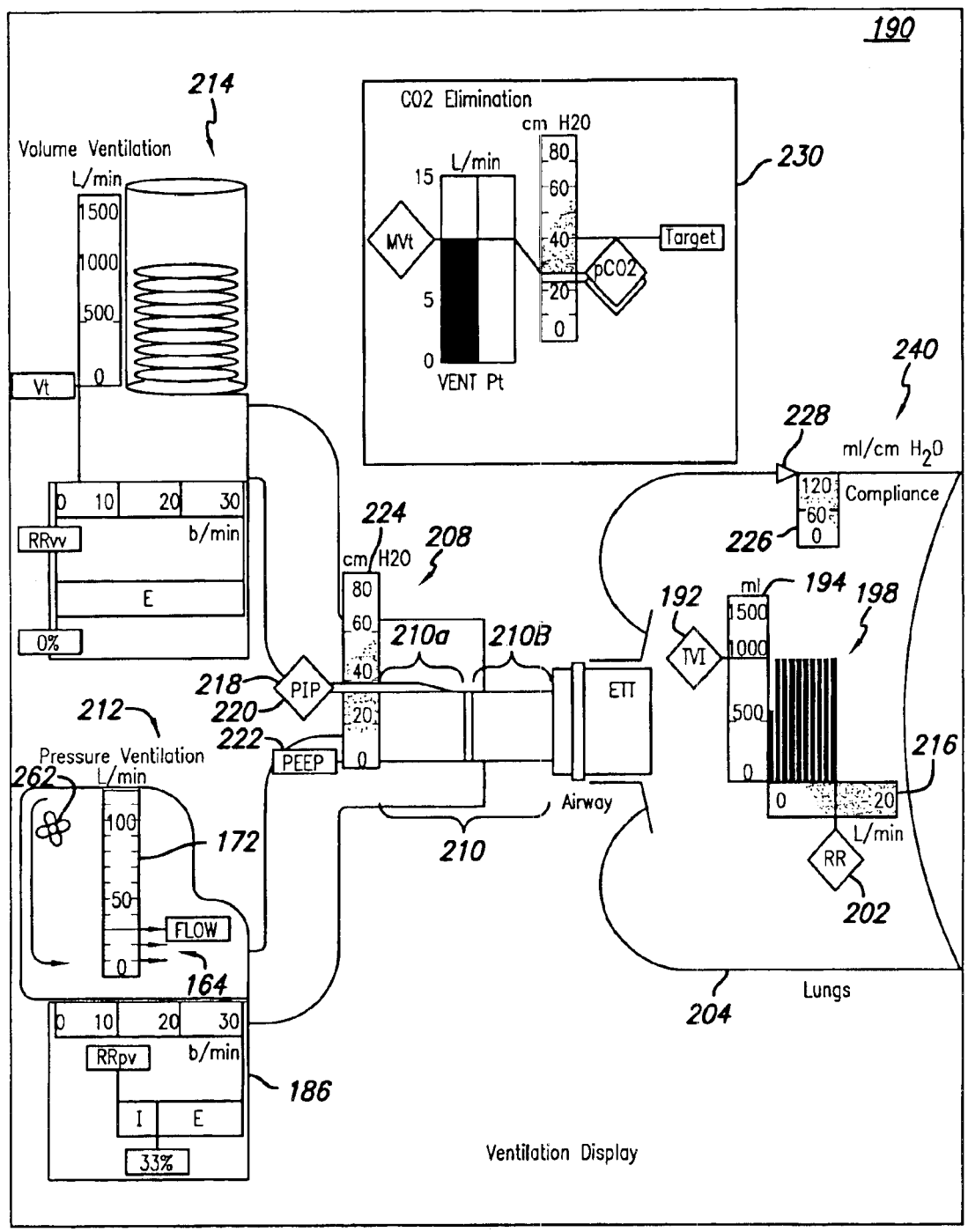
FIG. 11 shows one embodiment of a mixed ventilator/lung object.
Figure 12:
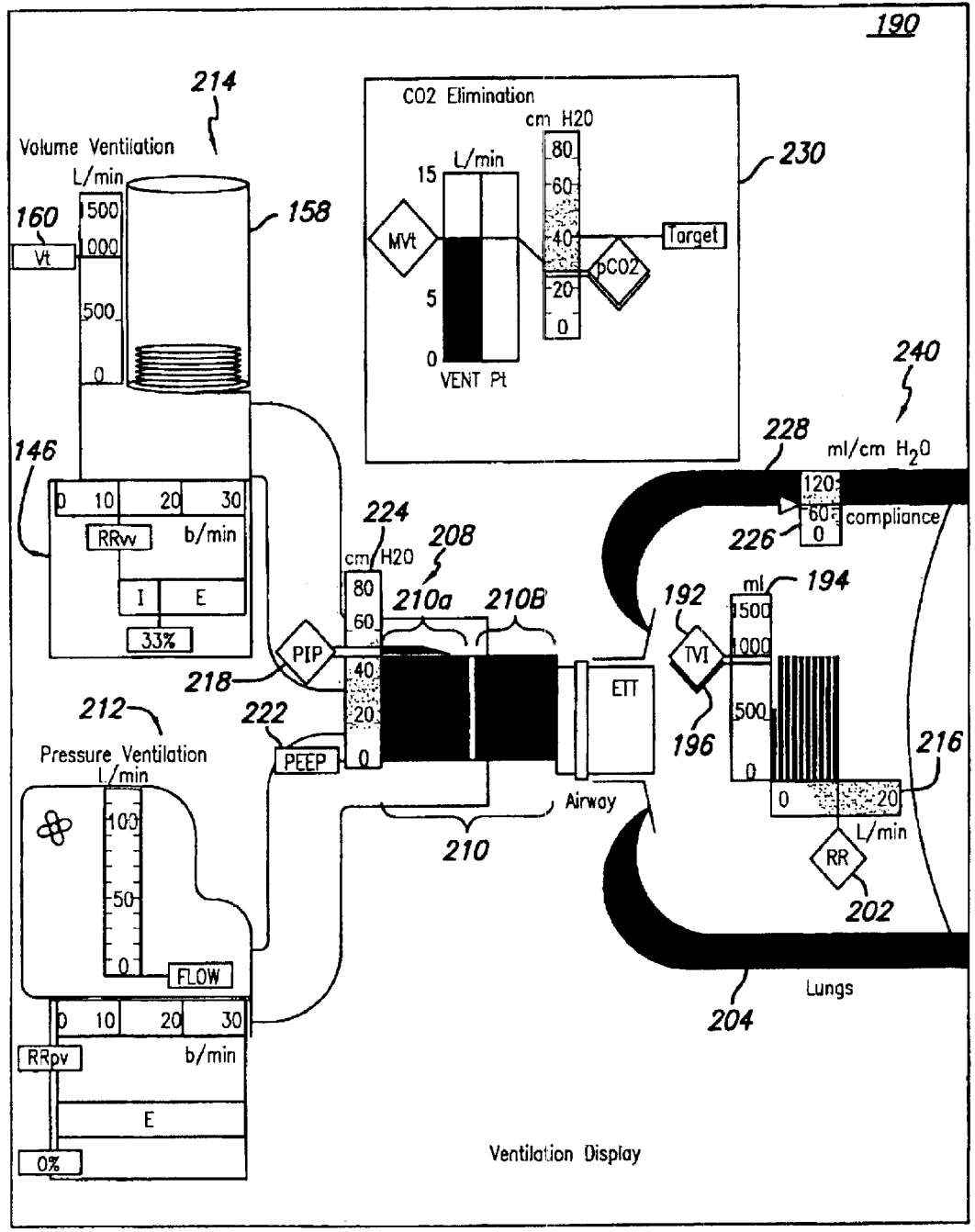
FIG. 12 shows another embodiment of the mixed ventilator/lung object.
Figure 13:
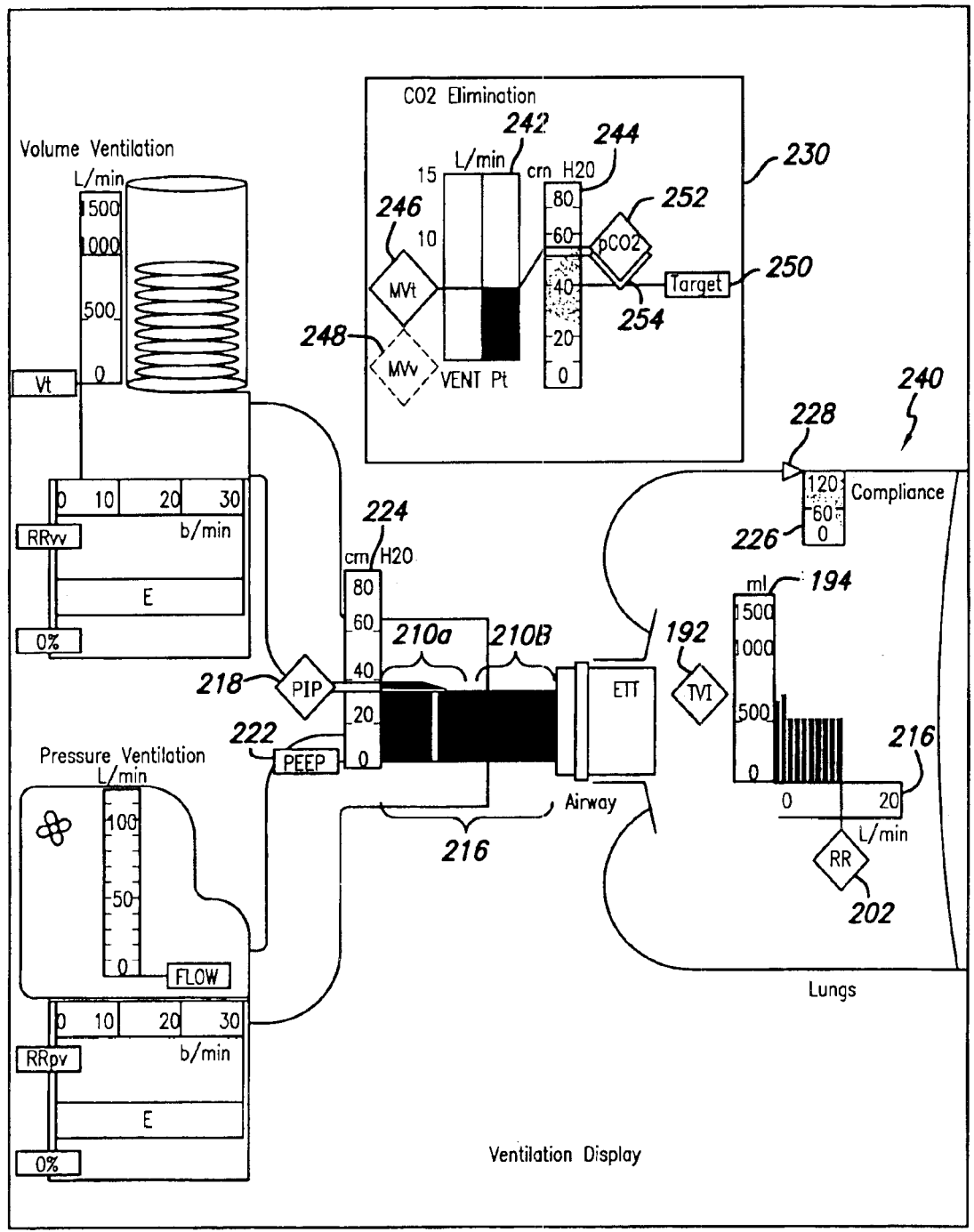
FIG. 13 shows another embodiment of the mixed ventilator object.

In FIGS. 11–13 are objects displaying information concerning airway resistance and ventilator data. In FIGS. 11–13, combined lung and ventilator object 190 displays information such as tidal volume inspired ("TVI"), tidal volume expired ("TVE"), respiratory rate ("RR"), peak inspiratory pressure ("PIP"), positive end respiratory pressure ("PEEP"), lung compliance, information on $CO_2$ elimination, and information as to both pressure and volume ventilators.

Inside combined lung and ventilator object 190 is lung object 240. Lung object 240 provides physicians with information concerning TVI and TVE (located behind the TVI diamond when TVI and TVE are the same) which are displayed by diamond shaped markers 192 (TVI) and 196 (TVE)(Not shown in FIG. 11). Markers 192 and 196 move up and down meter 194 and displays to a physician the amount of air inhaled and exhaled by a patient. As shown at 198, each breath for a total duration of a minute (longer intervals can be displayed) are displayed at 198 between meter 194 and 216. Meter 216, forming an X-axis, measures respiratory rate ("RR") which is measured in breaths per minute. As shown in FIG. 11, 10 breaths are displayed by vertically oriented columns 198 located above meter 216 which provides for an RR of 10 breaths/minute. Each breath is represented by a an elongated, vertically oriented column. There are a series of columns 198, each of which conveys certain information to a physician. For example, the first column at 198 shows that the first breath had a TVI and a TVE of slightly above a volume of 500 ml. All other subsequent breaths had TVI and TVE of 1000 ml. The object can also display discrepancies between TVI and TVE. For example, in FIG. 12, the second breath shows a slightly lower TVE than TVI. This difference between TVI and TVE might indicate that air is being lost possibly through a leak in tubing or even a hole in the lung.

Lung object 240 is surrounded by a pair of curved outer boundaries 204 which represent the lungs. In FIG. 11, it is a thin boundary and represents a normal lung. However, in FIG. 12, outer boundaries 204 are thickened and represent diseased noncompliant lungs. Located adjacent the upper boundary 204 is meter 226 which measures compliance of the lungs. In FIG. 11, which illustrates compliant lungs, compliance is shown to be slightly above 120 ml/cm $H_2O$. However, in FIG. 12, which shows a noncompliant lung, lung compliance is shown to be slightly above 60 ml/cm $H_2O$.

Upstream from lung object 240 is an airway resistance object 208 which conveys information to a physician or user concerning resistance in the respiratory tract. Airway resistance object 208 uses a "pipe" shaped metaphor to convey information concerning resistance to air inspiration and expiration in the respiratory tract. Part of the pipe shaped metaphor, section 210, contracts or levels off depending on whether blockage or resistance is encountered. For example, in FIGS. 11 and 12, section 210b is contracted or narrowed and could represent a bronchospasm, mucous plug or a tube with a kink. Located within airway resistance object 208 are PIP, mean airway pressure ("MAP") (not shown) and PEEP indicators which, in the same manner as the ventilator state object of FIG. 9, display values for these parameters. Diamond marker 218 displays the PIP value on meter 224. Diamond marker 220 displays Pplateau (behind the PIP diamond) on meter 224. Rectangular marker 222 displays the PEEP value on meter 224. PEEP marker 222 is rectangular shaped rather than diamond shaped to indicate that it is a physician set parameter rather than a measured patient parameter. When the PIP minus Pplateau are large, as is the case when obstruction to airflow is present, the resistor object will show narrowing as in FIG. 13.

Pressure ventilator object 212 (see FIG. 11) is virtually the same as pressure ventilator object 144. Located within pressure ventilator object 212 is propeller object 262 which as shown in pressure ventilator object 144, rotates counter clockwise when there is flow of air from the pressure ventilator to the patient and is static and stationary where there is no air flow. Meter 172 and arrows 164 also display the amount to air flowing to the patient. The three horizontal lines indicate that there is 30 liters air/minute being directed to the patient. Below is meter 186, which like meter 146 in FIG. 9 as to the volume ventilator, displays information concerning RR and the ratio of inspiration to expiration time.

Above pressure object 212 is volume ventilator object 214. As shown in FIG. 11, the volume ventilator is turned off and this can be understood in that volume ventilator object 214 is in gray and all of the parameters indicate that it is turned off. However, in FIG. 12, pressure ventilator 212 is turned off and volume ventilator 214 is turned on. However, as mentioned before, there are mixed volume-pressure ventilators. In Ventilator and Lung Object 190, were the patient receiving air from a mixed ventilator, both the volume ventilator object 214 and the pressure ventilator object 212 would be on and indicated as being operational.

In FIG. 12, volume ventilator object 214 is indicated as being on. Like the volume ventilator object of FIG. 11, volume ventilator object 214 has a bellows object 158 which indicates the volume of air the patient is receiving (the volume ventilator shows volume per breath on its scale and the pressure ventilator shows flow in L/min). Below volume ventilator 214 is box 146 which, like in FIG. 9, displays information concerning RR and inspiration and expiration time and I:E ratio.

Located above the lung object 210 is $CO_2$ elimination object 230. For example, in FIG. 13, $CO_2$ elimination object displays information concerning $CO_2$ elimination in real time. Meter 242 displays information concerning minute ventilation total ("MVt") as represented by marker 246 and minute ventilation ventilator ("MVv") as represented by marker 248. The left portion of meter 242 is shaded to represent how much $CO_2$ is eliminated by the ventilator (MVv) and the right portion of mater 242 demonstrates how much $CO_2$ is being eliminated by the patient. MVt marker gives the total $CO_2$ eliminated. The difference between MVt and MVv provides the amount of $CO_2$ eliminated by the patient.

Next to meter 242 is meter 244 which provides information concerning target $CO_2$ elimination value (as noted by marker 250), measured partial pressure $CO_2$ ("$pCO_2$") and measured exhaled $CO_2$ values ("Et $CO_2$"). $pCO_2$ values are noted by marker 252 and $EtCO_2$ values are noted by marker 254. Such values can be obtained from a spirometer. Differences between $pCO_2$ and $EtCO_2$ values can be an indicator of certain types of disease.

Meter 244 moves up and down in the Y direction depending on the $pCO_2$ and Et $CO_2$ values. The position of meter 244 along the Y axis and the position of markers 252 and 254 in relation to the MVt reading of 242 visually indicates excessive ventilation.

Figures 1, 14:
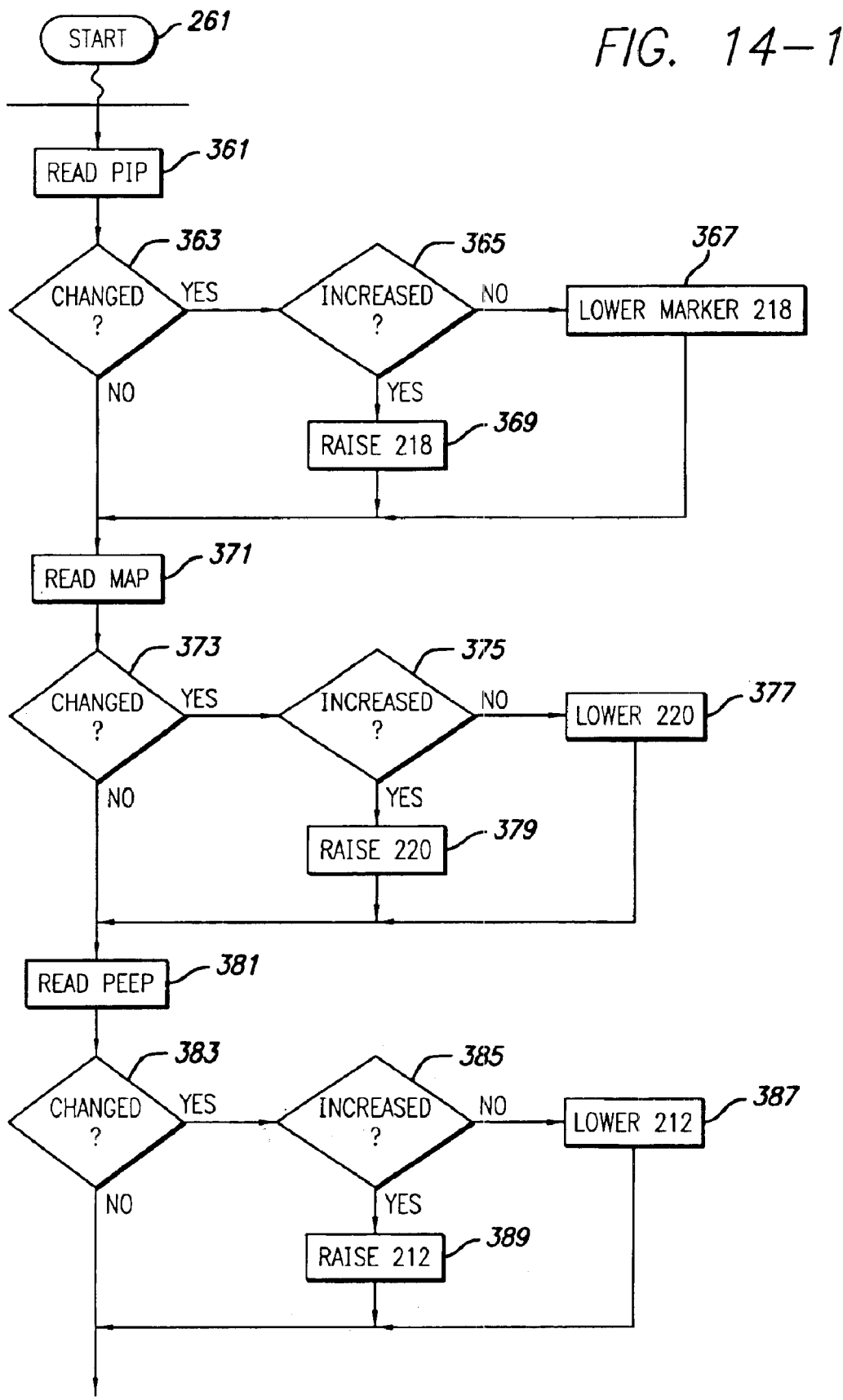
FIG. 14 shows one method of updating the mixed ventilator/lung object.
Figures 2, 14:
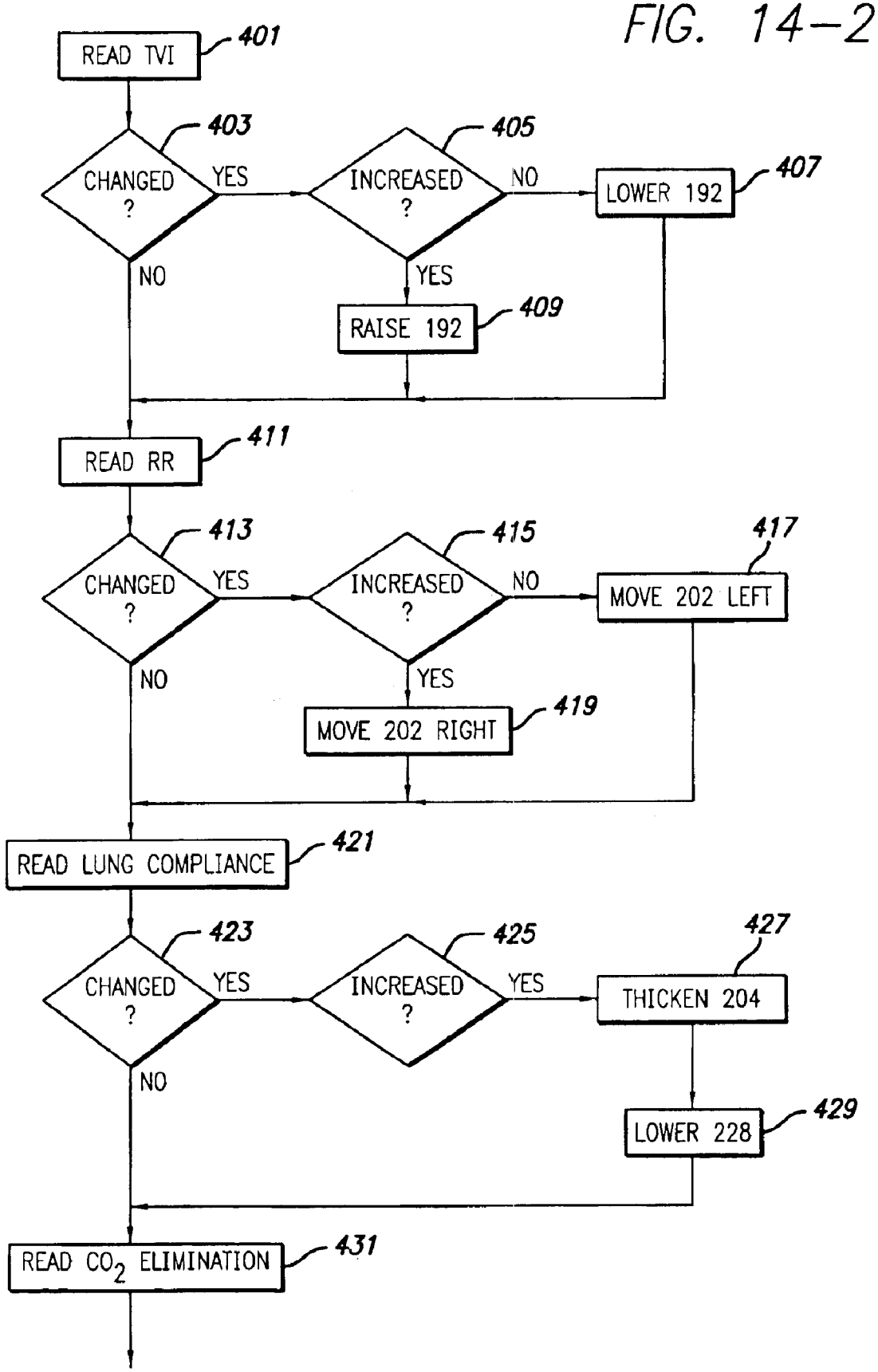
Figures 3, 14:
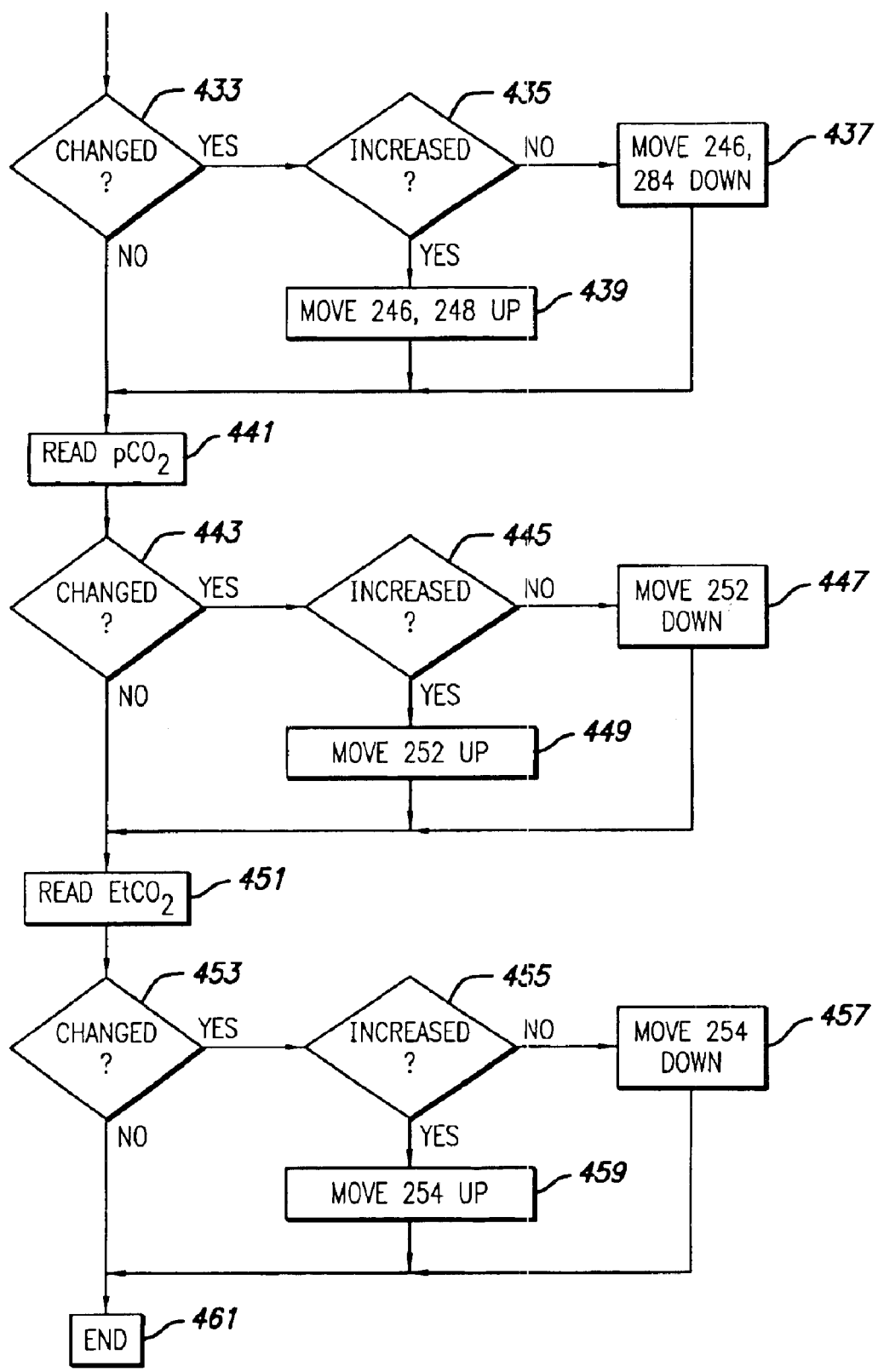

In FIG. 14, the process of updating the Combined Lung and Ventilator Object 190 is much the same as that of updating the Ventilator State Object 140 and therefore all of the steps will not be repeated here. When the process moves to updating lung object 210, the process moves to state 361 to read PIP. The process then moves to state 363 to determined whether PIP has changed from the last reading. If it has not, the process moves to state 371. However, if PIP has changed, the process moves to state 365 to determine whether PIP has increased or decreased. If PIP has decreased, the process moves to state 367 and lowers marker 218 to the appropriate PIP value on scale 224. However, if PIP has increased, the process moves to state 369 where marker 218 is raised above marker 220 which also raises a portion 210a of pipe shaped metaphor 210 to raise level 210a above 210b and gives the "pipe" an expanded appearance.

The process then moves to state 371 where MAP is read. The process moves to state 373 where it is determined whether MAP has changed since its last reading. If MAP has changed, the process then moves to state 375 where it is determined whether MAP has increased or decreased. If MAP has decreased, the process moves to state 377 where MAP marker 220 is lowered along meter 224 to the appropriate setting. However, if it is determined at state 375 that MAP has increased, the state moves to state 379 where MAP marker 220 is raised along meter 224 to the corresponding MAP value.

The process then moves to state 381 where PEEP is read. The process then moves to state 383 to determine whether PEEP has changed since its last reading. If it is determined that PEEP has changed, the process moves to state 385 to determine whether PEEP has increased or decreased. If it is determined that PEEP has decreased, the process moves to state 387 where PEEP marker 212 is lowered along meter 224 to the appropriate setting. If it is determined that PEEP has increased, the process moves to state 389 where PEEP marker 212 is raised to the appropriate setting along meter 224.

The process then moves to state 401 where total volume inspired ("TVI") is read. The process then moves to state 403 where it is determined whether TVI has changed since its last reading If it is determined that TVI has changed, the process moves to state 405 where it is determined whether TVI has increased or decreased. If it is determined that TVI has decreased, the process moves to state 407 where TVI marker 192 is lowered along meter 194. If it is determined that TVI has increased, the process is moved to state 409 where marker 192 is raised along meter 194 and the corresponding TVI reading is indicated.

The process then moves to state 411 where respiratory rate ("RR") is read. If process then moves to state 413 where it is determined whether RR has changed. If it is determined that RR has changed, the process moves to state 415 where it is determined whether RR has increased or decreased. If the RR has decreased, the process then moves to state 417 where the process moves RR marker 202 to the left. If the process determines that RR has increased, the process moves to state 419 where RR marker 202 is moved to the right to reflect the accurate RR reading.

The process then moves to state 421 where lung compliance is read. The process then moves to state 423 where it is determined whether lung compliance has changed. If lung compliance has changed, the process moves to state 425 to determine whether lung compliance has increased or decreased. If lung compliance has decreased, the process then moves to state 427 and scale 226 is updated and arrow 228 is moved to reflect the accurate lung compliance measurement. The process then moves the process to state 429 where the process enlarges i.e. thickens outer lung boundaries 204 to illustrate that the lungs have poor compliance. If the process determines that lung compliance has increased, the process moves to state 431 where scale 226 is updated to reflect the accurate lung compliance measurement.

The process then moves to state 431 where $CO_2$ elimination information is read. The process then moves to state 433 where it is determined whether $CO_2$ has changed. If it has changed, the process moves to state 435 where it is determined whether $CO_2$ elimination has increased or decreased. If it has decreased, the process moves to state 437 where markers 246 or 248 are moved down meter 242 to the appropriate reading. If the process determines that $CO_2$ elimination has increased, the process moves to state 439 and markers 246 and 248 are moved upward to the appropriate reading.

The process then moves to state 441 where pCO$_2$ is read. The process then moves to state 443 to determine whether pCO$_2$ has changed. If it has changed, the process then moves to state 445 where the process determines whether pCO$_2$ has increased or decreased. If pCO$_2$ has decreased, process moves to state 447 where marker 252 is moved down meter 244. If pCO$_2$ has increased, the process moves to state 449 and marker 252 moves up meter 244.

The process then moves to state 451 where EtCO$_2$ values are read. The process then moves to state 453 where it is determined whether EtCO$_2$ values have changed. If EtCO$_2$ values have changed, the process moves to state 455 where it is determined whether EtCO$_2$ values have increased or decreased. If the process determined that EtCO$_2$ values have decreased, the process moves to state 457 and marker 254 is moved down meter 244. If the process determines that EtCO$_2$ values have increased, the process moves to state 459 and marker 254 moves up meter 244. The process then moves to end state 461.

F. Oxygenation Object

Figure 15:
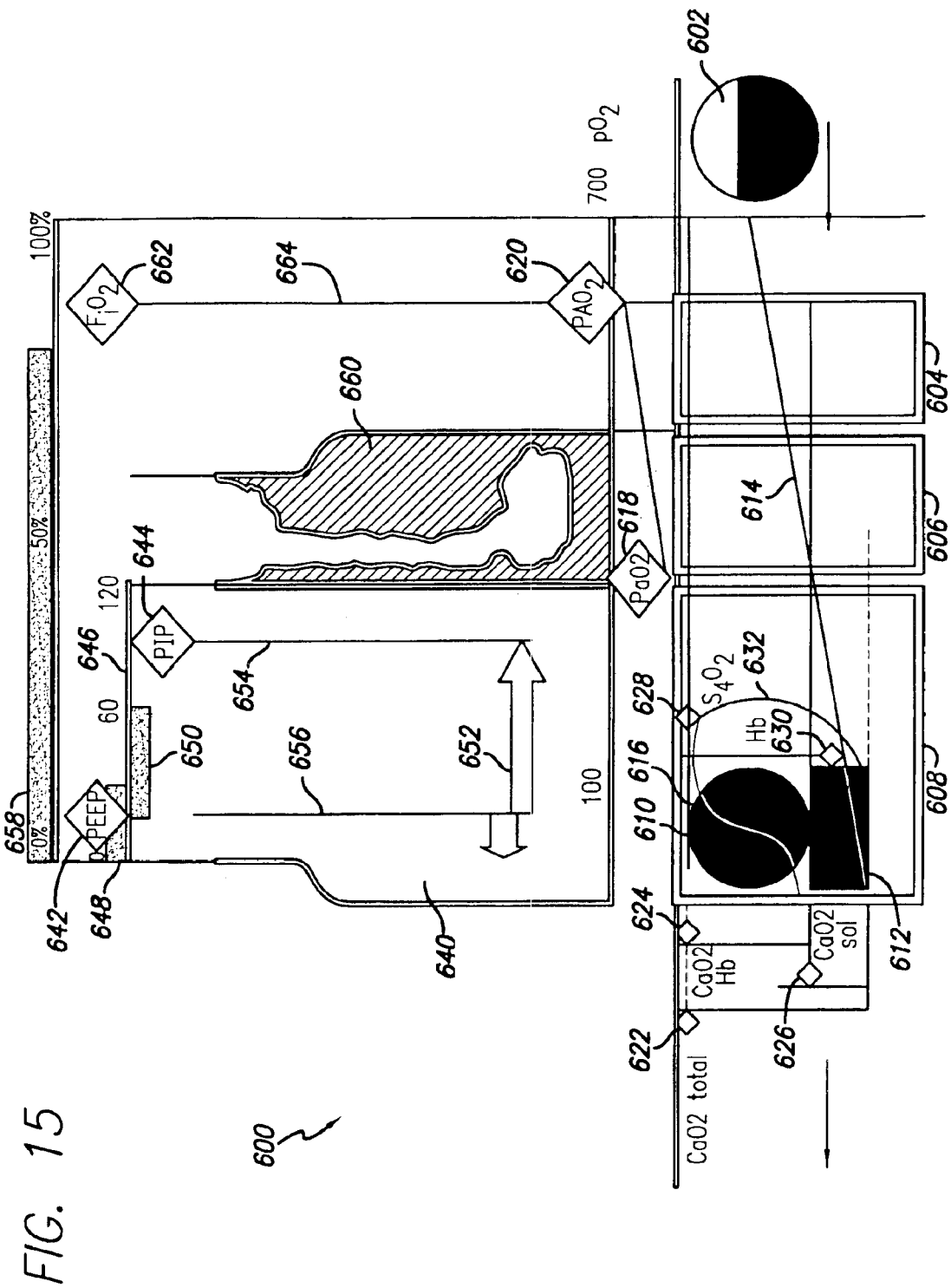
FIG. 15 shows one embodiment of an oxygenation object.

FIG. 15 illustrates an Oxygenation Object 600 which displays information relating to oxygenation of the blood and the state of lung tissue. Red blood cell object 602 is shown prior to being oxygenated by the lungs (flow, as indicated by the arrows, is from right to left). Boxes 604, 606 and 608 represent cross sections of blood vessels in the lung. Boxes 604, 606 and 608 can narrow or widen based on the difference between PaO$_2$ (marker 618) and PaO$_2$ (marker 620). Located within box 608 is red blood cell object 610 and soluble oxygenation object 612. Soluble oxygenation object 612 shows the concentration of oxygen in the plasma which can be influenced by a liquid such as perflubron based OXYGENT, a soluble oxygen carrier of Alliance Pharmaceutical Corp. Soluble oxygenation object 612 can increase in size depending on the contribution of soluble oxygenation of the blood. Linking soluble oxygenation object 612 and red blood cell object 602 is soluble O$_2$ line 614. The slope of line 614 can change based upon the level of soluble oxygenation of the blood. Where there is little or no oxygen solubility of the blood, the line levels out to a more horizontal slope.

Red blood cell object 610, which is intersected by an oxy-hemoglobin curve 616, visually indicates the level of hemoglobin and oxygenation of the arterial blood. CaO$_2$ total, represented by diamond 622 on the far left, represents the total arterial oxygenation of the blood. Marker 624 represents the amount of oxygenation of the blood by hemoglobin and marker 626 represents the amount of soluble oxygenation of the arterial blood. Both 624 and 626 move up and down in the Y direction as the respective values change. Marker 628 represents the arterial oxygen saturation (SaO$_2$) and 630 represents the hemoglobin ("Hb") concentration in the blood. Thus as the Hb value increases marker 630 moves to the right and the red blood cell object 610 increases in size and can reach the ideal size that is shown as circle 632.

Located above the red blood cell oxygenation portion of object 600 is the membrane portion of object 600 which illustrates physiological parameters as to oxygenation of the lung during ventilation and visual cues which indicate over ventilation of the lung. To the far left is lung object 640. Above lung object 640 is a marker 642 for positive end expiratory pressure ("PEEP") and a marker 644 for peak inspiratory pressure ("PIP"). Both PEEP marker 642 and PIP marker 644 move along X-oriented axis 646 to display the PIP and PEEP values. Adjacent PEEP and PIP markers are rectangular shaped objects 648 and 650 which are PEEP and PIP normal zones. When the PEEP or PIP marker 642 or 644 move beyond rectangular boxes 648 and 650 respectively, this indicates that the values are in a danger zone. For example, in FIG. 15, PIP marker 644 is beyond the PIP normal zone 650 and shows that it is in a danger zone. Below PIP and PEEP markers 642 and 644 is arrow 652 which shows the distance between PIP and PEEP values as further illustrated by vertically oriented lines 654 (extending downward from PIP marker 644) and line 656 descends from PEEP marker 642. As lines 654 and 656 separate, as further indicated by arrow 652, this visually cues the physician or other user that the patient might be in danger.

Adjacent lung object 640 is nonfunctional (collapsed or damaged) alveolus object 660. As shown in FIG. 15, nonfunctional alveolus object 660 is in a collapsed state which may be due to various diseases such as atelectases, postpneumonic states, etc. This further indicates that the current respirator settings need adjusting. Above lung object 640 and alveolar unit 660 is meter 658 which visually indicate the percentage of oxygen intake by the patient in real time. Below lung object 640 and dysfunctional alveolar unit 660 are PaO$_2$ and PAO$_2$ markers 618 and 620. Together these illustrate the alveolar arterial oxygen gradient and anatomic shunt. Markers 618 and 620 can move both in the X direction and provide important information as to oxygen intake. The movement of PaO$_2$ from left to right affects many of the other parameters of object 600. Above and linked to PAO$_2$ marker 620 is FiO$_2$ marker 662 which is linked to PAO$_2$ marker 620 by line 664 (the relationship between the FiO2 scale and the PO2 scale is through Charles Law).

Figures 1, 16:
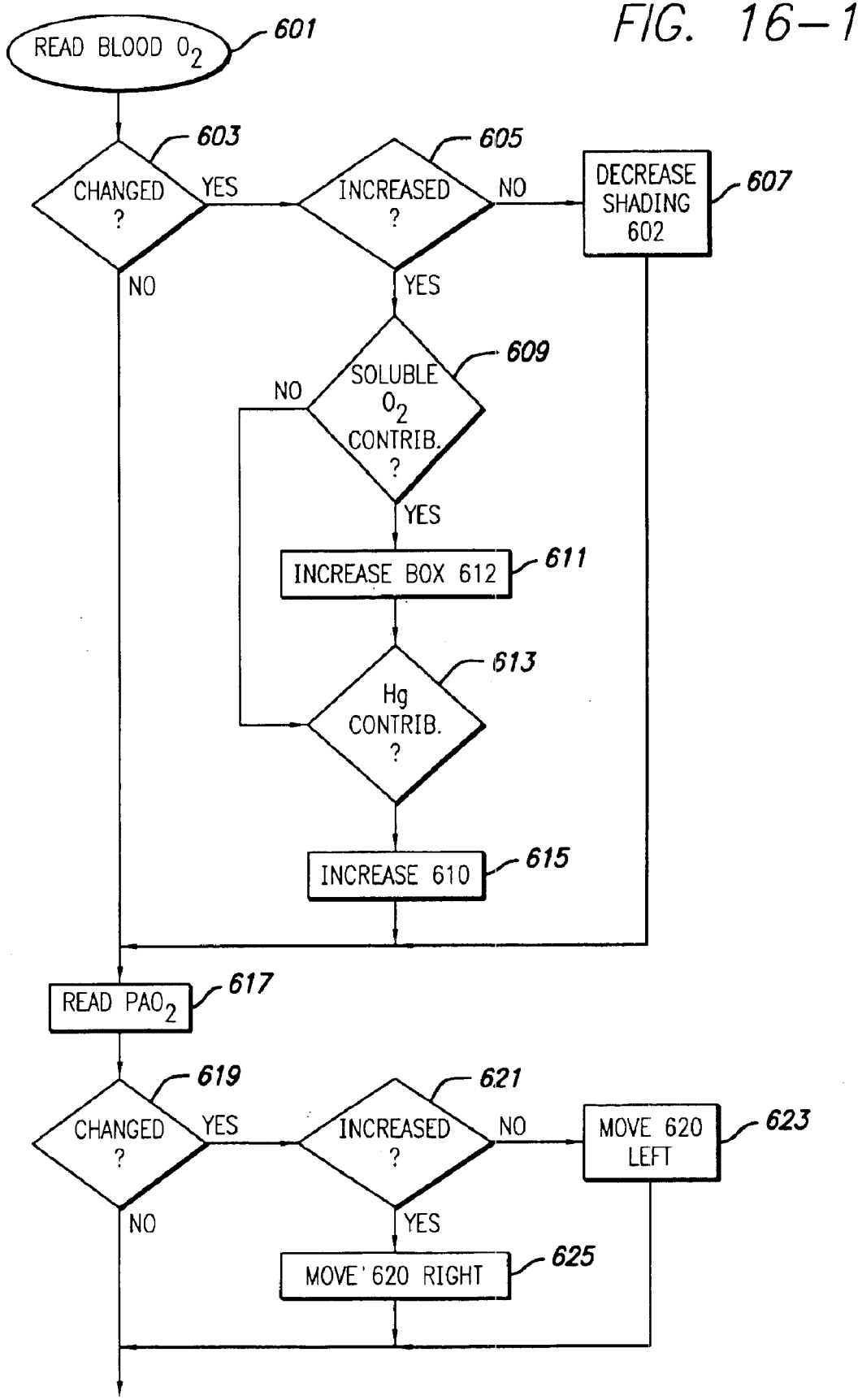
FIG. 16 is a flowchart of one method of updating the oxygenation object.
Figures 2, 16:
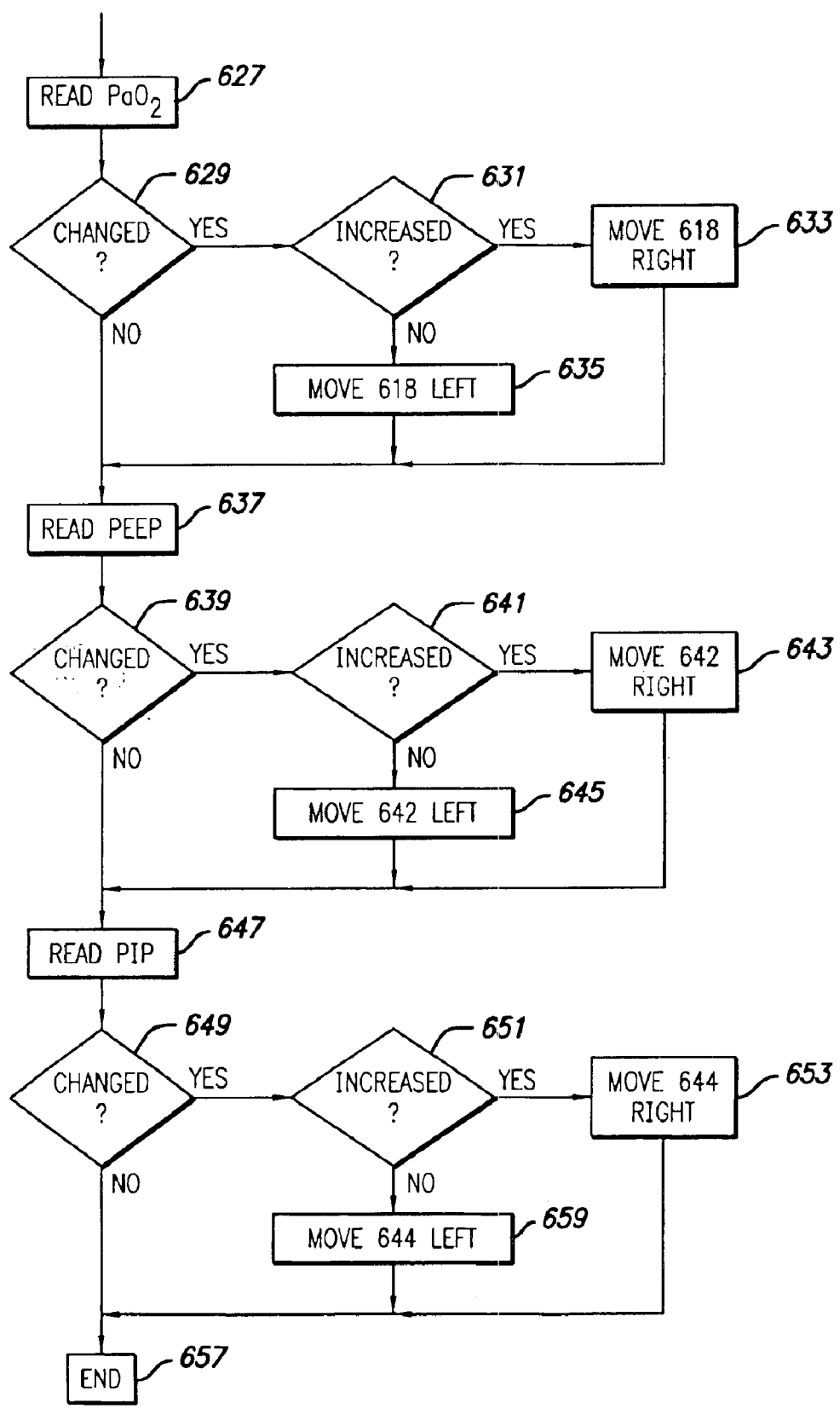

The process of updating object 600 is described in FIG. 16. The process reads the level of oxygenation of the blood at state 601 prior to oxygenation by the lungs. The process then moves to state 603 where it is determined whether the level of oxygenation of the blood has changed. If it is determined that the level of oxygenation has changed, the process then moves to state 605 where the process determines whether the level of oxygenation has increased or decreased. If it has decreased, the process then moves to state 607 the shading of object 602 is decreased. If it is determined at 605 that the level of oxygenation has increased, the process then moves to state 609 where the process determined whether there has been soluble oxygenation of the blood. If it is determined that there has been oxygenation of the blood by a soluble source, the size of box 612 is increased. If it is determined that there has been no contribution of a soluble oxygen carrier, the process then moves to state 613 where the hemoglobin concentration (i.e. oxygenation of the blood) is read the size of circle 610 is changed to reflect the Hg concentration in the blood. Markers 622, 624, 626, 628, 630 and the oxy-hemoglobin curve are all moved accordingly based wholly or in part on the Hg concentrations and oxygenation levels of the blood at this stage.

The process then moves to state 617 where PAO$_2$ is read. The process moves to state 619 where it is determined whether PAO$_2$ has changed. If it is determined that PAO$_2$ has changed, the process then moves to state 621 where it is determined whether PAO$_2$ has increased. If PAO$_2$ has increased, the process moves to state 623 where marker 620 is moved to the left. If it is determined that PAO$_2$ has decreased, the process moves to state 625 where 620 is moved to the right.

The process then moves to state 627 where PaO$_2$ is read. The process then moves to state 629 where it is determined whether PaO$_2$ has changed. If it is determined that PAO$_2$ has increased, the process then moves to state 633 where marker 618 is moved to the right. If the process determines that PaO₂ has decreased, marker 618 is moved to the left. Boxes 604, 606, 608 and alveolar object 660 can all change sizes based upon movement of PAO₂ and PaO₂

The process then moves to state 637 where PEEP is read. The process then moves to state 639 where it is determined whether PEEP has changed since its last reading. If it has changed, the process then moves to state 641 where it is determined whether PEEP has increased or decreased. If PEEP has increased the process then moves to state 643 where marker 642 is moved to the right. If PEEP has decreased, the process then moves to state 645 where marker 642 is moved to the left.

The process then moves to state 647 where PIP is read. The process then moves to state 649 where it is determined whether PIP has changed. If PIP has changed, the process moves to state 651 where it is determined whether PIP has increased or decreased. If PIP has increased, the process moves to state 653 where marker 644 is moved to the right. If PIP has been determined to have decreased, PIP marker 644 is moved to the left. The process then moves to end state 657.

What is claimed is:

1. A data object for visually displaying information of a ventilator in real time in a manner designed to minimize the cognitive steps required by a user to interpret the information, comprising: an object display wherein the object display is divided into at least one object for visually displaying information in real time concerning a volume ventilator and at least one object for visually displaying information in real time concerning a pressure ventilator and wherein the object display includes at least one, intuitive graphical representation or perceptual diagram of certain information.

2. The data object of claim 1 wherein the object display visually displays an oscillating bellows or a number of horizontally displaced lines for displaying information in real time as to volume of air flow to the patient.

3. The data object of claim 1 wherein horizontally oriented scales are utilized for displaying in real time information concerning the relationship between respiration rate, breath cycle time, inspiration time and expiration time.

4. The data object of claim 1 wherein information concerning PIP, MAP and PEEP is visually indicated by markers moving up and down a vertically oriented scale for displaying such information in real time.

5. The data object of claim 1 wherein the object display illustrates at least one emergent feature derived from the information and selected from the group consisting of the relationships of certain information to other information, presentation of certain information in context, relation of certain information to a frame of reference, the rate of change for certain information, and presentation of event information.

6. The data object of claim 5 wherein the object display visually displays an oscillating bellows or a number of horizontally displaced lines for displaying information in real time as to direction and volume of air flow to the patient.

7. The data object of claim 5 wherein horizontally oriented scales are utilized for displaying in real time information concerning the relationship between respiration rate, breath cycle time, inspiration time and expiration time.

8. The data object of claim 5 wherein information concerning PIP, MAP and PEEP is visually indicated by markers moving up and down a vertically oriented scale for displaying such information in real time.

9. The data object of claim 1, wherein the object display includes a visual representation of a valve that is closed when a patient is inspiring and open when the patient is expiring.

10. The data object of claim 5, wherein the object display includes a visual representation of a valve that is closed when a patient is inspiring and open when the patient is expiring.

11. A system for obtaining physiological information from a ventilator and displaying said information in real time in a manner designed to minimize the cognitive steps required by a user to interpret the information, comprising:

data acquisition means to acquire data relating to the ventilator and/or a patient connected to the ventilator;

a computer running software configured to map said acquired data onto a data object by relating a least one of said acquired data to at least one other of said acquired data wherein the data object includes at least one, intuitive graphical representation or perceptual diagram; and display means for displaying said data object wherein the object is divided into at least one object for visually displaying information in real time concerning a volume ventilator and at least one object for visually displaying information in real time concerning a pressure ventilator.

12. A system according to claim 11, wherein said data acquisition means is configured to acquire data selected from the group consisting of the mode of ventilation, ventilator settings, tidal volume, respiratory rate, peak inspiratory pressure, positive end expiratory pressure, Plataue pressure, End tidal carbon dioxide, and partial pressure.

13. A method for obtaining physiological information from a ventilator and displaying said information in real time in a manner designed to minimize the cognitive steps required by a user to interpret the information, said method comprising:

acquiring data relating to the ventilator and/or a patient connected to the ventilator;

mapping said acquired data onto a data object by relating at least one of said acquired data to at least one other of said acquired data, wherein the data object includes at least one, intuitive graphical representation or perceptual diagram; and displaying said data object, wherein the object is divided into at least one object for visually displaying information in real time concerning a volume ventilator and at least one object for visually displaying information in real time concerning a pressure ventilator.

14. A method according to claim 13, wherein the acquired data is selected from the group consisting of the mode of ventilation, ventilator settings, tidal volume, respiratory rate, peak inspiratory pressure, positive end expiratory pressure, plateau pressure, End tidal carbon dioxide, and partial pressure.

15. A method according to claim 14, wherein the step of mapping said data comprises comparing at least one of said acquired data with at least one other data.

* * * * *